(12) United States Patent
Haack et al.

(10) Patent No.: US 7,833,736 B2
(45) Date of Patent: Nov. 16, 2010

(54) PROTEIN MARKERS OF RESPONSIVENESS TO TYPE III RECEPTOR TYROSINE KINASE INHIBITORS

(75) Inventors: Herbert Haack, Holliston, MA (US); Laura Sullivan, Beverly, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 447 days.

(21) Appl. No.: 11/731,984

(22) Filed: Apr. 2, 2007

(65) Prior Publication Data

US 2009/0081709 A1   Mar. 26, 2009

Related U.S. Application Data

(60) Provisional application No. 60/788,172, filed on Mar. 31, 2006.

(51) Int. Cl.
    *G01N 33/574* (2006.01)
(52) U.S. Cl. ................................................ 435/7.23
(58) Field of Classification Search ................ None
    See application file for complete search history.

(56) References Cited

U.S. PATENT DOCUMENTS

| | | | |
|---|---|---|---|
| 5,443,962 A | 8/1995 | Draetta et al. | |
| 6,218,136 B1 | 4/2001 | Kumar et al. | |
| 2003/0129606 A1 | 7/2003 | Davis et al. | |
| 2003/0143582 A1 | 7/2003 | Reed et al. | |
| 2004/0038323 A1 | 2/2004 | Zhan et al. | |
| 2004/0265938 A1* | 12/2004 | Remacle et al. | 435/7.92 |
| 2006/0019252 A1 | 1/2006 | Nakamura et al. | |

2006/0019256 A1   1/2006   Clarke et al.

FOREIGN PATENT DOCUMENTS

EP   1564305 A2   8/2005

OTHER PUBLICATIONS

Tockman et al (Cancer Res., 1992, 52:2711s-2718s).*
Malusecka et al (Anticancer Research, 2001, 21:1015-1022).*
Zoumpourlis et al (Oncogene, 2000, 19:4011-4021).*
Petti et al., "Temporal quantification of mutant Kit tyrosine kinase signaling attenuated by a novel thiophene kinase inhibitor," OSI-930' Mol. Cancer Ther. 4(8): 1186-1197 (Aug. 2005) USA.
Palancade et al., "Investigating RNA polymerase II carboxyl-terminal domain (CTD) phosphorylation," Eur. J. Biochem 270: 3859-3870 (2003) Paris, France.
Raught et al., "Phosphorylation of eukaryotic translation initiation factor 4B Ser422 is modulated by S6 kinases," EMBO Journal 23: 1761-1769 (2004) USA.
Dai et al., "The kinase haspin is required for mitotic histone HE Thr3 phosphorylation and normal metaphase chromosome alignment," Genes & Development 19: 472-488 (2005) USA.

* cited by examiner

*Primary Examiner*—Laura B Goddard
(74) *Attorney, Agent, or Firm*—Nancy Chiu Wilker

(57) ABSTRACT

The invention discloses ten (10) protein markers predictive of cancer resistance or responsiveness to Type III Receptor Tyrosine Kinase (RTK) inhibitors, and provides methods for identifying a cancer that is likely to be resistant to a Type III RTK-inhibiting therapeutic by examining expression and/or activity of one or more of the disclosed biomarkers in a biological sample from the cancer. Methods for identifying a compound that inhibits a cancer resistant to a Type III RTK-inhibiting therapeutic by determining the effect of the compound on one or more of the disclosed marker proteins are also provided.

17 Claims, 13 Drawing Sheets

Figure 1. Xenografts models used for identifying predictive biomarkers for OSI-930.

| Responsive | | Resistant | |
|---|---|---|---|
| H209 | SCLC | ES2 | Ovarian |
| WBA | SCLC | MeWo | Melanoma |
| HCT116 | Colorectal | SK-MEL-5 | Melanoma |
| LS180 | Colorectal | Caki | RCC |
| DLD1 | Colorectal | H1975 | NSCLC |
| SW48 | Colorectal | BxPC3-A1 | Pancreatic |
| HT29 | Colorectal | | |
| COLO205 | Colorectal | | |
| KB | Head and Neck | | |
| Calu-6 | Lung | | |
| H526 | SCLC | | |
| Rxf-631 | RCC | | |

Figure 2. Unsupervised cluster analysis of IHC results based upon 200 antibodies and 18 xenograft models (resistant xenograft model cluster is highlighted).
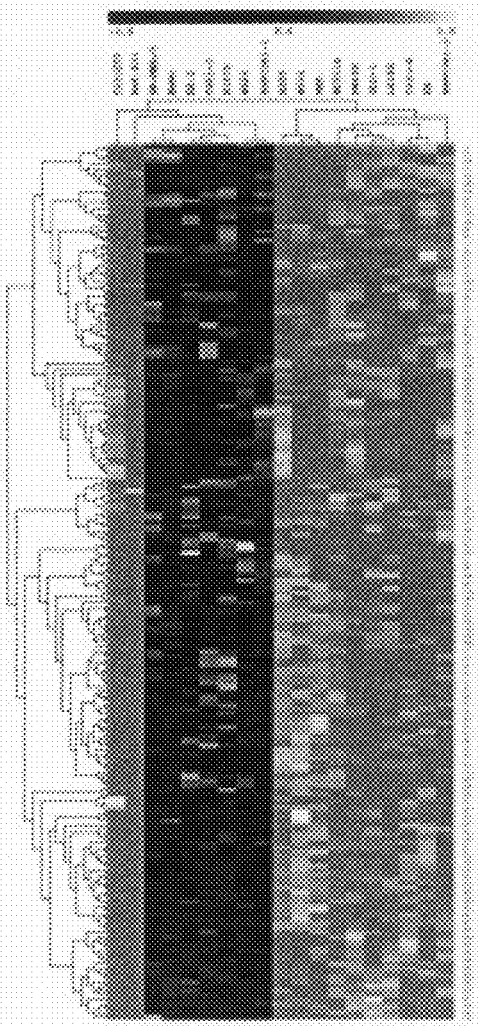

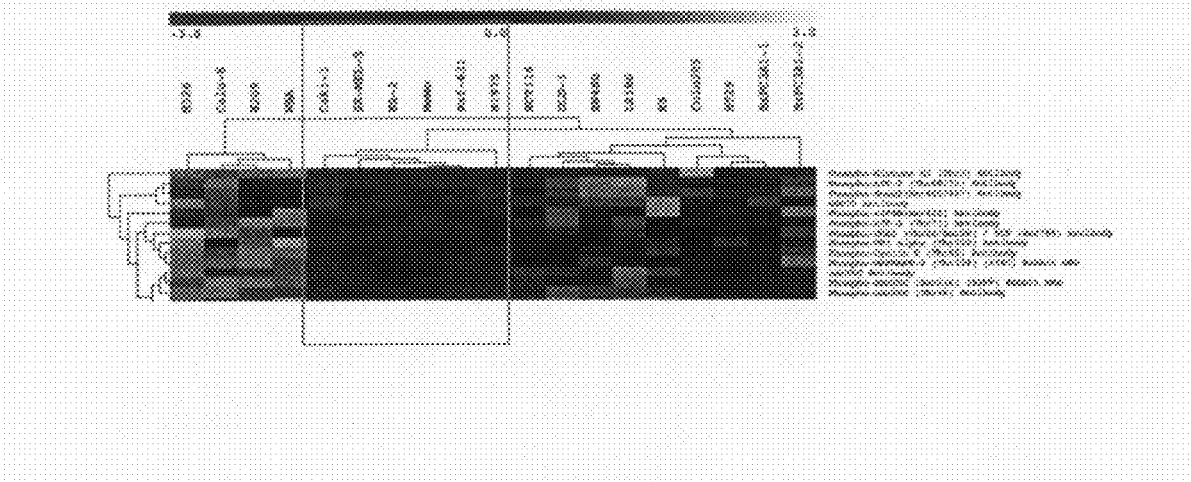
Figure 3. Supervised cluster analysis of IHC results identifies 11 markers predictive of response to OSI-930 and similar drugs.

Figure 4. Amino acid sequence of HSP27.

MTERRVPFSL LRGPSWDPFR DWYPHSRLFD QAFGLPRLPE
EWSQWLGGSS WPGYVRPLPP AAIESPAVAA PAYSRALSRQ
LSSGVSEIRH TADRWRVSLD VNHFAPDELT VKTKDGVVEI
TGKHEERQDE HGYISRCFTR KYTLPPGVDP TQVSSSLSPE
GTLTVEAPMP KLATQSNEIT IPVTFESRAQ LGGPEAAKSD ETAAK

Figure 5. Amino acid sequence of cortactin.

MWKASAGHAV SIAQDDAGAD DWETDPDFVN DVSEKEQRWG
AKTVQGSGHQ EHINIHKLRE NVFQEHQTLK EKELETGPKA
SHGYGGKFGV EQDRMDKSAV GHEYQSKLSK HCSQVDSVRG
FGGKFGVQMD RVDQSAVGFE YQGKTEKHAS QKDYSSGFGG
KYGVQADRVD KSAVGFDYQG KTEKHESQRD YSKGFGGKYG
IDKDKVDKSA VGFEYQGKTE KHESQKDYVK GFGGKFGVQT
DRQDKCALGW DHQEKLQLHE SQKDYKTGFG GKFGVQSERQ
DSAAVGFDYK EKLAKHESQQ DYSKGFGGKY GVQKDRMDKN
ASTFEDVTQV SSAYQKTVPV EAVTSKTSNI RANFENLAKE
KEQEDRRKAE AERAQRMAKE RQEQEEARRK LEEQARAKTQ
TPPVSPAPQP TEERLPSSPV YEDAASFKAE LSYRGPVSGT
EPEPVYSMEA ADYREASSQQ GLAYATEAVY ESAEAPGHYP
AEDSTYDEYE NDLGITAVAL YDYQAAGDDE ISFDPDDIIT
NIEMIDDGWW RGVCKGRYGL FPANYVELRQ

Figure 6. Amino acid sequence of CDC25C.

MSTELFSSTR EEGSSGSGPS FRSNQRKMLN LLLERDTSFT
VCPDVPRTPV GKFLGDSANL SILSGGTPKC CLDLSNLSSG
EITATQLTTS ADLDETGHLD SSGLQEVHLA GMNHDQHLMK
CSPAQLLCST PNGLDRGHRK RDAMCSSSAN KENDNGNLVD
SEMKYLGSPI TTVPKLDKNP NLGEDQAEEI SDELMEFSLK
DQEAKVSRSG LYRSPSMPEN LNRPRLKQVE KFKDNTIPDK
VKKKYFSGQG KLRKGLCLKK TVSLCDITIT QMLEEDSNQG
HLIGDFSKVC ALPTVSGKHQ DLKYVNPETV AALLSGKFQG
LIEKFYVIDC RYPYEYLGGH IQGALNLYSQ EELFNFFLKK
PIVPLDTQKR IIIVFHCEFS SERGPRMCRC LREEDRSLNQ
YPALYYPELY ILKGGYRDFF PEYMELCEPQ SYCPMHHQDH
KTELLRCRSQ SKVQEGERQL REQIALLVKD MSP

Figure 7. Amino acid sequence of MAPKAPK2.

MLSNSQGQSP PVPFPAPAPP PQPPTPALPH PPAQPPPPPP
QQFPQFHVKS GLQIKKNAII DDYKVTSQVL GLGINGKVLQ
IFNKRTQEKF ALKMLQDCPK ARREVELHWR ASQCPHIVRI
VDVYENLYAG RKCLLIVMEC LDGGELFSRI QDRGDQAFTE
REASEIMKSI GEAIQYLHSI NIAHRDVKPE NLLYTSKRPN AILKLTDFGF
AKETTSHNSL TTPCYTPYYV APEVLGPEKY DKSCDMWSLG
VIMYILLCGY PPFYSNHGLA ISPGMKTRIR MGQYEFPNPE
WSEVSEEVKM LIRNLLKTEP TQRMTITEFM NHPWIMQSTK
VPQTPLHTSR VLKEDKERWE DVKEEMTSAL ATMRVDYEQI
KIKKIEDASN PLLLKRRKKA RALEAAALAH

Figure 8. Amino acid sequence of cyclin E.

MPRERRERDA KERDTMKEDG GAEFSARSRK RKANVTVFLQ

DPDEEMAKID RTARDQCGSQ PWDNNAVCAD PCSLIPTPDK

EDDDRVYPNS TCKPRIIAPS RGSPLPVLSW ANREEVWKIM

LNKEKTYLRD QHFLEQHPLL QPKMRAILLD WLMEVCEVYK

LHRETFYLAQ DFFDRYMATQ ENVVKTLLQL IGISSLFIAA KLEEIYPPKL

HQFAYVTDGA CSGDEILTME LMIMKALKWR LSPLTIVSWL

NVYMQVAYLN DLHEVLLPQY PQQIFIQIAE LLDLCVLDVD

CLEFPYGILA ASALYHFSSS ELMQKVSGYQ WCDIENCVKW

MVPFAMVIRE TGSSKLKHFR GVADEDAHNI QTHRDSLDLL

DKARAKKAML SEQNRASPLP SGLLTPPQSG KKQSSGPEMA

Figure 9. Amino acid sequence of stathmin.

AGTGTGGTCA GGCGGCTCGG ACTGAGCAGG ACTTTCCTTA
TCCCAGTTGA TTGTGCAGAA TACACTGCCT ATCGCTTGTC
TTCTATTCAC CATGGCTTCT TCTGATATCC AGGTGAAAGA
ACTGGAGAAG CGTGCCTCAG GCCAGGCTTT TGAGCTGATT
CTCAGCCCTC GGTCAAAAGA ATCTGTTCCA GAATTCCCCC
TTTCCCCTCC AAAGAAGAAG GATCTTTCCC TGGAGGAAAT
TCAGAAGAAA TTAGAAGCTG CAGAAGAAAG ACGCAAGTCC
CATGAAGCTG AGGTCTTGAA GCAGCTGGCT GAGAAACGAG
AGCACGAGAA AGAAGTGCTT CAGAAGGCAA TAGAAGAGAA
CAACAACTTC AGTAAAATGG CAGAAGAGAA ACTGACCCAC
AAAATGGAAG CTAATAAAGA GAACCGAGAG GCACAAATGG
CTGCCAAACT GGAACGTTTG CGAGAGAAGG ATAAGCACAT
TGAAGAAGTG CGGAAGAACA AGAATCCAA AGACCCTGCT
GACGAGACTG AAGCTGACTA ATTTGTTCTG AGAACTGACT
TTCTCCCCAT CCCCTTCCTA AATATCCAAA GACTGTACTG
GCCAGTGTCA TTTTATTTTT TCCCTCCTGA CAAATATTTT
AGAAGCTAAT GTAGGACTGT ATAGGTAGAT CCAGATCCAG
ACTGTAAGAT GTTGTTTTAG GGGCTAAAGG GGAGAAACTG
AAAGTGTTTT ACTCTTTTTC TAAAGTGTTG GTCTTTCTAA
TGTAGCTATT TTTCTTGTTG CATCTTTTCT ACTTCAGTAC
ACTTGGTGTA CTGGGTTAAT GGCTAGTACT GTATTGGCTC
TGTGAAAACA TATTTGTGAA AAGAGTATGT AGTGGCTTCT
TTTGAACTGT TAGATGCTGA ATATCTGTTC ACTTTTCAAT
CCCAATTCTG TCCCAATCTT ACCAGATGCT ACTGGACTTG
AATGGTTAAT AAAACTGCAC AGTGCTGTTG GTGGCAGTGA
CTTCTTTTGA GTTAGGTTAA TAAATCAAGC CATAGAGCCC
CTCCTGGTTG ATACTTGTTC CAGATGGGGC CTTTGGGGCT
GGTAGAAATA CCCAACGCAC AAATGACCGC ACGTTCTCTG
CCCCGTTTCT TGCCCCAGTG TGGTTTGCAT TGTCTCCTTC
CACAATGACT GCTTTGTTTG GATGCCTCAG CCCAGGTCAG
CTGTTACTTT CTTTCAGATG TTTATTTGCA AACAACCATT
TTTTGTTCTG TGTCCCTTTT AAAAGGCAGA TTAAAAGCAC
AAGCGTGTTT CTAGAGAACA GTTGAGAGAG AATCTCAAGA
TTCTACTTGG TGGTTTGCTT GCTCTACGTT ACAGGTGGGG
CATGTCCTCA TCCTTTCCTG CCATAAAAGC TATGACACGA
GAATCAGAAT ATTAATAAAA CTTTATGTAC TGCTGT

Figure 10. Amino acid sequence of ATF-2

MKFKLHVNSA RQYKDLWNMS DDKPFLCTAP GCGQRFTNED
HLAVHKHKHE MTLKFGPARN DSVIVADQTP TPTRFLKNCE
EVGLFNELAS PFENEFKKAS EDDIKKMPLD LSPLATPIIR SKIEEPSVVE
TTHQDSPLPH PESTTSDEKE VPLAQTAQPT SAIVRPASLQ
VPNVLLTSSD SSVIQQAVP SPTSSTVITQ APSSNRPIVP
VPGPFPLLLH LPNGQTMPVA IPASITSSNV HVPAAVPLVR
PVTMVPSVPG IPGPSSPQPV QSEAKMRLKA ALTQQHPPVT
NGDTVKGHGS GLVRTQSEES RPQSLQQPAT STTETPASPA
HTTPQTQSTS GRRRRAANED PDEKRRKFLE RNRAAASRCR
QKRKVWVQSL EKKAEDLSSL NGQLQSEVTL LRNEVAQLKQ
LLLAHKDCPV TAMQKKSGYH TADKDDSSED ISVPSSPHTE
AIQHSSVSTS NGVSSTSKAE AVATSVLTQM ADQSTEPALS
QIVMAPSSQS QPSGS

Figure 11. Amino acid sequence of histone H3.

MARTKQTARK STGGKAPRKQ LATKVARKSA PATGGVKKPH
RYRPGTVALR EIRRYQKSTE LLIRKLPFQR LMREIAQDFK
TDLRFQSSAV MALQEACESY LVGLFEDTNL CVIHAKRVTI
MPKDIQLARR IRGERA

Figure 12. Amino acid sequence of EIF-4B.

MAASAKKKNK KGKTISLTDF LAEDGGTGGG STYVSKPVSW
ADETDDLEGD VSTTWHSNDD DVYRAPPIDR SILPTAPRAA
REPNIDRSRL PKSPPYTAFL GNLPYDVTEE SIKEFFRGLN
ISAVRLPREP SNPERLKGFG YAEFEDLDSL LSALSLNEES
LGNRRIRVDV ADQAQDKDRD DRSFGRDRNR DSDKTDTDWR
ARPATDSFDD YPPRRGDDSF GDKYRDRYDS DRYRDGYRDG
YRDGPRRDMD RYGGRDRYDD RGSRDYDRGY DSRIGSGRRA
FGSGYRRDDD YRGGGDRYED RYDRRDDRSW SSRDDYSRDD
YRRDDRGPPQ RPKLNLKPRS TPEEDDSSAS TSQSTRAASI
FGGAKPVDTA AREREVEERL QKEQEKLQRQ WNEPKLERRP
RERHPSWRSE ETQERERSRT GSESSQTGTS TTSSRNARRR
ESEKSLENET LNKEEDCHSP TSKPPKPDQP LKVMPAPPPK
ENAWVKRSSN PPARSQSSDT EQQSPTSGGG KVAPAQPSEE
GPGRKDENKV DGMNAPKGQT GNSSRGPGDG GNRDHWKESD
RKDGKKDQDS RSAPEPKKPE ENPASKFSSA SKYAALSVDG
EDENEGEDYA E

Figure 13. Amino acid sequence of Rpb1.

MHGGGPPSGD SACPLRTIKR VQFGVLSPDE LKRMSVTEGG
IKYPETTEGG RPKLGGLMDP RQGVIERTGR CQTCAGNMTE
CPGHFGHIEL AKPVFHVGFL VKTMKVLRCV CFFCSKLLVD SNNPKIKDIL
AKSKGQPKKR LTHVYDLCKG KNICEGGEEM DNKFGVEQPE
GDEDLTKEKG HGGCGRYQPR IRRSGLELYA EWKHVNEDSQ
EKKILLSPER VHEIFKRISD EECFVLGMEP RYARPEWMIV TVLPVPPLSV
RPAVVMQGSA RNQDDLTHKL ADIVKINNQL RRNEQNGAAA
HVIAEDVKLL QFHVATMVDN ELPGLPRAMQ KSGRPLKSLK
QRLKGKEGRV RGNLMGKRVD FSARTVITPD PNLSIDQVGV
PRSIAANMTF AEIVTPFNID RLQELVRRGN SQYPGAKYII RDNGDRIDLR
FHPKPSDLHL QTGYKVERHM CDGDIVIFNR QPTLHKMSMM
GHRVRILPWS TFRLNLSVTT PYNADFDGDE MNLHLPQSLE
TRAEIQELAM VPRMIVTPQS NRPVMGIVQD TLTAVRKFTK RDVFLERGEV
MNLLMFLSTW DGKVPQPAIL KPRPLWTGKQ IFSLIIPGHI NCIRTHSTHP
DDEDSGPYKH ISPGDTKVVV ENGELIMGIL CKKSLGTSAG SLVHISYLEM
GHDITRLFYS NIQTVINNWL LIEGHTIGIG DSIADSKTYQ DIQNTIKKAK
QDVIEVIEKA HNNELEPTPG NTLRQTFENQ VNRILNDARD KTGSSAQKSL
SEYNNFKSMV VSGAKGSKIN ISQVIAVVGQ QNVEGKRIPF GFKHRTLPHF
IKDDYGPESR GFVENSYLAG LTPTEFFFHA MGGREGLIDT AVKTAETGYI
QRRLIKSMES VMVKYDATVR NSINQVVQLR YGEDGLAGES
VEFQNLATLK PSNKAFEKKF RFDYTNERAL RRTLQEDLVK DVLSNAHIQN
ELEREFERMR EDREVLRVIF PTGDSKVVLP CNLLRMIWNA QKIFHINPRL
PSDLHPIKVV EGVKELSKKL VIVNGDDPLS RQAQENATLL FNIHLRSTLC
SRRMAEEFRL SGEAFDWLLG EIESKFNQAI AHPGEMVGAL
AAQSLGEPAT QMTLNTFHYA GVSAKNVTLG VPRLKELINI SKKPKTPSLT
VFLLGQSARD AERAKDILCR LEHTTLRKVT ANTAIYYDPN PQSTVVAEDQ
EWVNVYYEMP DFDVARISPW LLRVELDRKH MTDRKLTMEQ
IAEKINAGFG DDLNCIFNDD NAEKLVLRIR IMNSDENKMQ EEEEVVDKMD
DDVFLRCIES NMLTDMTLQG IEQISKVYMH LPQTDNKKKI IITEDGEFKA
LQEWILETDG VSLMRVLSEK DVDPVRTTSN DIVEIFTVLG IEAVRKALER
ELYHVISFDG SYVNYRHLAL LCDTMTCRGH LMAITRHGVN
RQDTGPLMKC SFEETVDVLM EAAAHGESDP MKGVSENIML
GQLAPAGTGC FDLLLDAEKC KYGMEIPTNI PGLGAAGPTG
MFFGSAPSPM GGISPAMTPW NQGATPAYGA WSPSVGSGMT
PGAAGFSPSA ASDASGFSPG YSPAWSPTPG SPGSPGPSSP
YIPSPGGAMS PSYSPTSPAY EPRSPGGYTP QSPSYSPTSP
SYSPTSPSYS PTSPNYSPTS PSYSPTSPSY SPTSPSYSPT SPSYSPTSPS
YSPTSPSYSP TSPSYSPTSP SYSPTSPSYS PTSPSYSPTS PSYSPTSPSY
SPTSPSYSPT SPSYSPTSPS YSPTSPNYSP TSPNYTPTSP SYSPTSPSYS
PTSPNYTPTS PNYSPTSPSY SPTSPSYSPT SPSYSPSSPR
YTPQSPTYTP SSPSYSPSSP SYSPTSPKYT PTSPSYSPSS PEYTPTSPKY
SPTSPKYSPT SPKYSPTSPT YSPTTPKYSP TSPTYSPTSP VYTPTSPKYS
PTSPTYSPTS PKYSPTSPTY SPTSPKGSTY SPTSPGYSPT SPTYSLTSPA
ISPDDSDEEN

SEQUENCE LISTING

```
<160> NUMBER OF SEQ ID NOS: 10

<210> SEQ ID NO 1
<211> LENGTH: 205
<212> TYPE: PRT
<213> ORGANISM: Homo sapiens

<400> SEQUENCE: 1

Met Thr Glu Arg Arg Val Pro Phe Ser Leu Leu Arg Gly Pro Ser Trp
 1               5                   10                  15

Asp Pro Phe Arg Asp Trp Tyr Pro His Ser Arg Leu Phe Asp Gln Ala
```

-continued

```
                    20                  25                  30
Phe Gly Leu Pro Arg Leu Pro Glu Glu Trp Ser Gln Trp Leu Gly Gly
             35                  40                  45

Ser Ser Trp Pro Gly Tyr Val Arg Pro Leu Pro Ala Ala Ile Glu
 50                  55                  60

Ser Pro Ala Val Ala Ala Pro Ala Tyr Ser Arg Ala Leu Ser Arg Gln
 65                  70                  75                  80

Leu Ser Ser Gly Val Ser Glu Ile Arg His Thr Ala Asp Arg Trp Arg
                 85                  90                  95

Val Ser Leu Asp Val Asn His Phe Ala Pro Asp Glu Leu Thr Val Lys
                100                 105                 110

Thr Lys Asp Gly Val Val Glu Ile Thr Gly Lys His Glu Glu Arg Gln
            115                 120                 125

Asp Glu His Gly Tyr Ile Ser Arg Cys Phe Thr Arg Lys Tyr Thr Leu
            130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
            195                 200                 205

<210> SEQ ID NO 2
<211> LENGTH: 550
<212> TYPE: PRT
<213> ORGANISM: Homo sapiens

<400> SEQUENCE: 2

Met Trp Lys Ala Ser Ala Gly His Ala Val Ser Ile Ala Gln Asp Asp
  1               5                  10                  15

Ala Gly Ala Asp Asp Trp Glu Thr Asp Pro Asp Phe Val Asn Asp Val
                 20                  25                  30

Ser Glu Lys Glu Gln Arg Trp Gly Ala Lys Thr Val Gln Gly Ser Gly
             35                  40                  45

His Gln Glu His Ile Asn Ile His Lys Leu Arg Glu Asn Val Phe Gln
 50                  55                  60

Glu His Gln Thr Leu Lys Glu Lys Glu Leu Glu Thr Gly Pro Lys Ala
 65                  70                  75                  80

Ser His Gly Tyr Gly Gly Lys Phe Gly Val Glu Gln Asp Arg Met Asp
                 85                  90                  95

Lys Ser Ala Val Gly His Glu Tyr Gln Ser Lys Leu Ser Lys His Cys
            100                 105                 110

Ser Gln Val Asp Ser Val Arg Gly Phe Gly Gly Lys Phe Gly Val Gln
            115                 120                 125

Met Asp Arg Val Asp Gln Ser Ala Val Gly Phe Glu Tyr Gln Gly Lys
130                 135                 140

Thr Glu Lys His Ala Ser Gln Lys Asp Tyr Ser Ser Gly Phe Gly Gly
145                 150                 155                 160

Lys Tyr Gly Val Gln Ala Asp Arg Val Asp Lys Ser Ala Val Gly Phe
                165                 170                 175

Asp Tyr Gln Gly Lys Thr Glu Lys His Glu Ser Gln Arg Asp Tyr Ser
            180                 185                 190
```

```
Lys Gly Phe Gly Gly Lys Tyr Gly Ile Asp Lys Asp Lys Val Asp Lys
        195                 200                 205
Ser Ala Val Gly Phe Glu Tyr Gln Gly Lys Thr Glu Lys His Glu Ser
        210                 215                 220
Gln Lys Asp Tyr Val Lys Gly Phe Gly Gly Lys Phe Gly Val Gln Thr
225                 230                 235                 240
Asp Arg Gln Asp Lys Cys Ala Leu Gly Trp Asp His Gln Glu Lys Leu
                245                 250                 255
Gln Leu His Glu Ser Gln Lys Asp Tyr Lys Thr Gly Phe Gly Gly Lys
            260                 265                 270
Phe Gly Val Gln Ser Glu Arg Gln Asp Ser Ala Ala Val Gly Phe Asp
            275                 280                 285
Tyr Lys Glu Lys Leu Ala Lys His Glu Ser Gln Gln Asp Tyr Ser Lys
        290                 295                 300
Gly Phe Gly Gly Lys Tyr Gly Val Gln Lys Asp Arg Met Asp Lys Asn
305                 310                 315                 320
Ala Ser Thr Phe Glu Asp Val Thr Gln Val Ser Ser Ala Tyr Gln Lys
                325                 330                 335
Thr Val Pro Val Glu Ala Val Thr Ser Lys Thr Ser Asn Ile Arg Ala
            340                 345                 350
Asn Phe Glu Asn Leu Ala Lys Glu Lys Glu Gln Glu Asp Arg Arg Lys
        355                 360                 365
Ala Glu Ala Glu Arg Ala Gln Arg Met Ala Lys Glu Arg Gln Glu Gln
        370                 375                 380
Glu Glu Ala Arg Arg Lys Leu Glu Glu Gln Ala Arg Ala Lys Thr Gln
385                 390                 395                 400
Thr Pro Pro Val Ser Pro Ala Pro Gln Pro Thr Glu Glu Arg Leu Pro
                405                 410                 415
Ser Ser Pro Val Tyr Glu Asp Ala Ala Ser Phe Lys Ala Glu Leu Ser
            420                 425                 430
Tyr Arg Gly Pro Val Ser Gly Thr Glu Pro Glu Pro Val Tyr Ser Met
        435                 440                 445
Glu Ala Ala Asp Tyr Arg Glu Ala Ser Ser Gln Gln Gly Leu Ala Tyr
        450                 455                 460
Ala Thr Glu Ala Val Tyr Glu Ser Ala Glu Ala Pro Gly His Tyr Pro
465                 470                 475                 480
Ala Glu Asp Ser Thr Tyr Asp Glu Tyr Glu Asn Asp Leu Gly Ile Thr
                485                 490                 495
Ala Val Ala Leu Tyr Asp Tyr Gln Ala Ala Gly Asp Asp Glu Ile Ser
            500                 505                 510
Phe Asp Pro Asp Asp Ile Ile Thr Asn Ile Glu Met Ile Asp Asp Gly
        515                 520                 525
Trp Trp Arg Gly Val Cys Lys Gly Arg Tyr Gly Leu Phe Pro Ala Asn
        530                 535                 540
Tyr Val Glu Leu Arg Gln
545                 550

<210> SEQ ID NO 3
<211> LENGTH: 473
<212> TYPE: PRT
<213> ORGANISM: Homo sapiens

<400> SEQUENCE: 3

Met Ser Thr Glu Leu Phe Ser Ser Thr Arg Glu Glu Gly Ser Ser Gly
  1               5                  10                  15
```

-continued

```
Ser Gly Pro Ser Phe Arg Ser Asn Gln Arg Lys Met Leu Asn Leu Leu
         20                  25                  30

Leu Glu Arg Asp Thr Ser Phe Thr Val Cys Pro Asp Val Pro Arg Thr
         35                  40                  45

Pro Val Gly Lys Phe Leu Gly Asp Ser Ala Asn Leu Ser Ile Leu Ser
         50                  55                  60

Gly Gly Thr Pro Lys Cys Cys Leu Asp Leu Ser Asn Leu Ser Ser Gly
65                   70                  75                  80

Glu Ile Thr Ala Thr Gln Leu Thr Thr Ser Ala Asp Leu Asp Glu Thr
                 85                  90                  95

Gly His Leu Asp Ser Ser Gly Leu Gln Glu Val His Leu Ala Gly Met
         100                 105                 110

Asn His Asp Gln His Leu Met Lys Cys Ser Pro Ala Gln Leu Leu Cys
         115                 120                 125

Ser Thr Pro Asn Gly Leu Asp Arg Gly His Arg Lys Arg Asp Ala Met
         130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                 165                 170                 175

Asp Lys Asn Pro Asn Leu Gly Glu Asp Gln Ala Glu Glu Ile Ser Asp
         180                 185                 190

Glu Leu Met Glu Phe Ser Leu Lys Asp Gln Glu Ala Lys Val Ser Arg
         195                 200                 205

Ser Gly Leu Tyr Arg Ser Pro Ser Met Pro Glu Asn Leu Asn Arg Pro
         210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                 245                 250                 255

Cys Leu Lys Lys Thr Val Ser Leu Cys Asp Ile Thr Ile Thr Gln Met
         260                 265                 270

Leu Glu Glu Asp Ser Asn Gln Gly His Leu Ile Gly Asp Phe Ser Lys
         275                 280                 285

Val Cys Ala Leu Pro Thr Val Ser Gly Lys His Gln Asp Leu Lys Tyr
         290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                 325                 330                 335

Leu Gly Gly His Ile Gln Gly Ala Leu Asn Leu Tyr Ser Gln Glu Glu
         340                 345                 350

Leu Phe Asn Phe Phe Leu Lys Lys Pro Ile Val Pro Leu Asp Thr Gln
         355                 360                 365

Lys Arg Ile Ile Ile Val Phe His Cys Glu Phe Ser Ser Glu Arg Gly
         370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                 405                 410                 415

Arg Asp Phe Phe Pro Glu Tyr Met Glu Leu Cys Glu Pro Gln Ser Tyr
         420                 425                 430
```

```
Cys Pro Met His His Gln Asp His Lys Thr Glu Leu Leu Arg Cys Arg
            435                 440                 445

Ser Gln Ser Lys Val Gln Glu Gly Glu Arg Gln Leu Arg Glu Gln Ile
        450                 455                 460

Ala Leu Leu Val Lys Asp Met Ser Pro
465                 470

<210> SEQ ID NO 4
<211> LENGTH: 400
<212> TYPE: PRT
<213> ORGANISM: Homo sapiens

<400> SEQUENCE: 4

Met Leu Ser Asn Ser Gln Gly Gln Ser Pro Pro Val Pro Phe Pro Ala
  1               5                  10                  15

Pro Ala Pro Pro Gln Pro Thr Pro Ala Leu Pro His Pro Pro
             20                  25                  30

Ala Gln Pro Pro Pro Pro Gln Gln Phe Pro Gln Phe His Val
             35                  40                  45

Lys Ser Gly Leu Gln Ile Lys Lys Asn Ala Ile Ile Asp Asp Tyr Lys
         50                  55                  60

Val Thr Ser Gln Val Leu Gly Leu Gly Ile Asn Gly Lys Val Leu Gln
 65                  70                  75                  80

Ile Phe Asn Lys Arg Thr Gln Glu Lys Phe Ala Leu Lys Met Leu Gln
                 85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
            115                 120                 125

Ala Gly Arg Lys Cys Leu Leu Ile Val Met Glu Cys Leu Asp Gly Gly
            130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
            180                 185                 190

Leu Tyr Thr Ser Lys Arg Pro Asn Ala Ile Leu Lys Leu Thr Asp Phe
        195                 200                 205

Gly Phe Ala Lys Glu Thr Thr Ser His Asn Ser Leu Thr Thr Pro Cys
210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn
        275                 280                 285

Pro Glu Trp Ser Glu Val Ser Glu Glu Val Lys Met Leu Ile Arg Asn
    290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335
```

```
His Thr Ser Arg Val Leu Lys Glu Asp Lys Glu Arg Trp Glu Asp Val
            340                 345                 350

Lys Glu Glu Met Thr Ser Ala Leu Ala Thr Met Arg Val Asp Tyr Glu
            355                 360                 365

Gln Ile Lys Ile Lys Ile Glu Asp Ala Ser Asn Pro Leu Leu Leu
            370                 375             380

Lys Arg Arg Lys Lys Ala Arg Ala Leu Glu Ala Ala Leu Ala His
385                 390                 395                 400
```

<210> SEQ ID NO 5
<211> LENGTH: 410
<212> TYPE: PRT
<213> ORGANISM: Homo sapiens

<400> SEQUENCE: 5

```
Met Pro Arg Glu Arg Arg Glu Arg Asp Ala Lys Glu Arg Asp Thr Met
  1               5                  10                  15

Lys Glu Asp Gly Gly Ala Glu Phe Ser Ala Arg Ser Arg Lys Arg Lys
                20                  25                  30

Ala Asn Val Thr Val Phe Leu Gln Asp Pro Asp Glu Glu Met Ala Lys
            35                  40                  45

Ile Asp Arg Thr Ala Arg Asp Gln Cys Gly Ser Gln Pro Trp Asp Asn
    50                  55                  60

Asn Ala Val Cys Ala Asp Pro Cys Ser Leu Ile Pro Thr Pro Asp Lys
 65                  70                  75                  80

Glu Asp Asp Asp Arg Val Tyr Pro Asn Ser Thr Cys Lys Pro Arg Ile
                85                  90                  95

Ile Ala Pro Ser Arg Gly Ser Pro Leu Pro Val Leu Ser Trp Ala Asn
            100                 105                 110

Arg Glu Glu Val Trp Lys Ile Met Leu Asn Lys Glu Lys Thr Tyr Leu
        115                 120                 125

Arg Asp Gln His Phe Leu Glu Gln His Pro Leu Leu Gln Pro Lys Met
    130                 135                 140

Arg Ala Ile Leu Leu Asp Trp Leu Met Glu Val Cys Glu Val Tyr Lys
145                 150                 155                 160

Leu His Arg Glu Thr Phe Tyr Leu Ala Gln Asp Phe Phe Asp Arg Tyr
                165                 170                 175

Met Ala Thr Gln Glu Asn Val Val Lys Thr Leu Leu Gln Leu Ile Gly
            180                 185                 190

Ile Ser Ser Leu Phe Ile Ala Ala Lys Leu Glu Glu Ile Tyr Pro Pro
        195                 200                 205

Lys Leu His Gln Phe Ala Tyr Val Thr Asp Gly Ala Cys Ser Gly Asp
    210                 215                 220

Glu Ile Leu Thr Met Glu Leu Met Ile Met Lys Ala Leu Lys Trp Arg
225                 230                 235                 240

Leu Ser Pro Leu Thr Ile Val Ser Trp Leu Asn Val Tyr Met Gln Val
                245                 250                 255

Ala Tyr Leu Asn Asp Leu His Glu Val Leu Leu Pro Gln Tyr Pro Gln
            260                 265                 270

Gln Ile Phe Ile Gln Ile Ala Glu Leu Leu Asp Leu Cys Val Leu Asp
        275                 280                 285

Val Asp Cys Leu Glu Phe Pro Tyr Gly Ile Leu Ala Ala Ser Ala Leu
    290                 295                 300

Tyr His Phe Ser Ser Ser Glu Leu Met Gln Lys Val Ser Gly Tyr Gln
```

```
                305                 310                 315                 320
Trp Cys Asp Ile Glu Asn Cys Val Lys Trp Met Val Pro Phe Ala Met
                    325                 330                 335
Val Ile Arg Glu Thr Gly Ser Ser Lys Leu Lys His Phe Arg Gly Val
                340                 345                 350
Ala Asp Glu Asp Ala His Asn Ile Gln Thr His Arg Asp Ser Leu Asp
            355                 360                 365
Leu Leu Asp Lys Ala Arg Ala Lys Leu Ala Met Leu Ser Glu Gln Asn
        370                 375                 380
Arg Ala Ser Pro Leu Pro Ser Gly Leu Leu Thr Pro Pro Gln Ser Gly
385                 390                 395                 400
Lys Lys Gln Ser Ser Gly Pro Glu Met Ala
                405                 410

<210> SEQ ID NO 6
<211> LENGTH: 149
<212> TYPE: PRT
<213> ORGANISM: Homo sapiens

<400> SEQUENCE: 6

Met Ala Ser Ser Asp Ile Gln Val Lys Glu Leu Glu Lys Arg Ala Ser
1               5                   10                  15
Gly Gln Ala Phe Glu Leu Ile Leu Ser Pro Arg Ser Lys Glu Ser Val
            20                  25                  30
Pro Glu Phe Pro Leu Ser Pro Pro Lys Lys Asp Leu Ser Leu Glu
        35                  40                  45
Glu Ile Gln Lys Lys Leu Glu Ala Ala Glu Glu Arg Arg Lys Ser His
    50                  55                  60
Glu Ala Glu Val Leu Lys Gln Leu Ala Glu Lys Arg Glu His Glu Lys
65                  70                  75                  80
Glu Val Leu Gln Lys Ala Ile Glu Glu Asn Asn Asn Phe Ser Lys Met
                85                  90                  95
Ala Glu Glu Lys Leu Thr His Lys Met Glu Ala Asn Lys Glu Asn Arg
            100                 105                 110
Glu Ala Gln Met Ala Ala Lys Leu Glu Arg Leu Arg Glu Lys Asp Lys
        115                 120                 125
His Ile Glu Glu Val Arg Lys Asn Lys Glu Ser Lys Asp Pro Ala Asp
    130                 135                 140
Glu Thr Glu Ala Asp
145

<210> SEQ ID NO 7
<211> LENGTH: 505
<212> TYPE: PRT
<213> ORGANISM: Homo sapiens

<400> SEQUENCE: 7

Met Lys Phe Lys Leu His Val Asn Ser Ala Arg Gln Tyr Lys Asp Leu
1               5                   10                  15
Trp Asn Met Ser Asp Asp Lys Pro Phe Leu Cys Thr Ala Pro Gly Cys
            20                  25                  30
Gly Gln Arg Phe Thr Asn Glu Asp His Leu Ala Val His Lys His Lys
        35                  40                  45
His Glu Met Thr Leu Lys Phe Gly Pro Ala Arg Asn Asp Ser Val Ile
    50                  55                  60
Val Ala Asp Gln Thr Pro Thr Pro Thr Arg Phe Leu Lys Asn Cys Glu
```

```
             65                  70                  75                  80
         Glu Val Gly Leu Phe Asn Glu Leu Ala Ser Pro Phe Glu Asn Glu Phe
                             85                  90                  95
         Lys Lys Ala Ser Glu Asp Asp Ile Lys Lys Met Pro Leu Asp Leu Ser
                            100                 105                 110
         Pro Leu Ala Thr Pro Ile Ile Arg Ser Lys Ile Glu Glu Pro Ser Val
                            115                 120                 125
         Val Glu Thr Thr His Gln Asp Ser Pro Leu Pro His Pro Glu Ser Thr
                            130                 135                 140
         Thr Ser Asp Glu Lys Glu Val Pro Leu Ala Gln Thr Ala Gln Pro Thr
         145                 150                 155                 160
         Ser Ala Ile Val Arg Pro Ala Ser Leu Gln Val Pro Asn Val Leu Leu
                            165                 170                 175
         Thr Ser Ser Asp Ser Ser Val Ile Ile Gln Gln Ala Val Pro Ser Pro
                            180                 185                 190
         Thr Ser Ser Thr Val Ile Thr Gln Ala Pro Ser Ser Asn Arg Pro Ile
                            195                 200                 205
         Val Pro Val Pro Gly Pro Phe Pro Leu Leu Leu His Leu Pro Asn Gly
         210                 215                 220
         Gln Thr Met Pro Val Ala Ile Pro Ala Ser Ile Thr Ser Ser Asn Val
         225                 230                 235                 240
         His Val Pro Ala Ala Val Pro Leu Val Arg Pro Val Thr Met Val Pro
                            245                 250                 255
         Ser Val Pro Gly Ile Pro Gly Pro Ser Ser Pro Gln Pro Val Gln Ser
                            260                 265                 270
         Glu Ala Lys Met Arg Leu Lys Ala Ala Leu Thr Gln Gln His Pro Pro
                            275                 280                 285
         Val Thr Asn Gly Asp Thr Val Lys Gly His Gly Ser Gly Leu Val Arg
                            290                 295                 300
         Thr Gln Ser Glu Glu Ser Arg Pro Gln Ser Leu Gln Gln Pro Ala Thr
         305                 310                 315                 320
         Ser Thr Thr Glu Thr Pro Ala Ser Pro Ala His Thr Thr Pro Gln Thr
                            325                 330                 335
         Gln Ser Thr Ser Gly Arg Arg Arg Ala Ala Asn Glu Asp Pro Asp
                            340                 345                 350
         Glu Lys Arg Arg Lys Phe Leu Glu Arg Asn Arg Ala Ala Ala Ser Arg
                            355                 360                 365
         Cys Arg Gln Lys Arg Lys Val Trp Val Gln Ser Leu Glu Lys Lys Ala
                            370                 375                 380
         Glu Asp Leu Ser Ser Leu Asn Gly Gln Leu Gln Ser Glu Val Thr Leu
         385                 390                 395                 400
         Leu Arg Asn Glu Val Ala Gln Leu Lys Gln Leu Leu Leu Ala His Lys
                            405                 410                 415
         Asp Cys Pro Val Thr Ala Met Gln Lys Lys Ser Gly Tyr His Thr Ala
                            420                 425                 430
         Asp Lys Asp Asp Ser Ser Glu Asp Ile Ser Val Pro Ser Ser Pro His
                            435                 440                 445
         Thr Glu Ala Ile Gln His Ser Ser Val Ser Thr Ser Asn Gly Val Ser
                            450                 455                 460
         Ser Thr Ser Lys Ala Glu Ala Val Ala Thr Ser Val Leu Thr Gln Met
         465                 470                 475                 480
         Ala Asp Gln Ser Thr Glu Pro Ala Leu Ser Gln Ile Val Met Ala Pro
                            485                 490                 495
```

```
Ser Ser Gln Ser Gln Pro Ser Gly Ser
        500             505

<210> SEQ ID NO 8
<211> LENGTH: 136
<212> TYPE: PRT
<213> ORGANISM: Homo sapiens

<400> SEQUENCE: 8

Met Ala Arg Thr Lys Gln Thr Ala Arg Lys Ser Thr Gly Gly Lys Ala
 1               5                  10                  15

Pro Arg Lys Gln Leu Ala Thr Lys Val Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Met Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ser Tyr Leu Val Gly Leu Phe Glu Asp Thr Asn Leu Cys Val
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 9
<211> LENGTH: 611
<212> TYPE: PRT
<213> ORGANISM: Homo sapiens

<400> SEQUENCE: 9

Met Ala Ala Ser Ala Lys Lys Lys Asn Lys Lys Gly Lys Thr Ile Ser
 1               5                  10                  15

Leu Thr Asp Phe Leu Ala Glu Asp Gly Gly Thr Gly Gly Gly Ser Thr
            20                  25                  30

Tyr Val Ser Lys Pro Val Ser Trp Ala Asp Glu Thr Asp Asp Leu Glu
        35                  40                  45

Gly Asp Val Ser Thr Thr Trp His Ser Asn Asp Asp Asp Val Tyr Arg
50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Glu Ser Ile
            100                 105                 110

Lys Glu Phe Phe Arg Gly Leu Asn Ile Ser Ala Val Arg Leu Pro Arg
        115                 120                 125

Glu Pro Ser Asn Pro Glu Arg Leu Lys Gly Phe Gly Tyr Ala Glu Phe
    130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175
```

```
Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Thr Asp Ser Phe
            195                 200                 205

Asp Asp Tyr Pro Pro Arg Arg Gly Asp Asp Ser Phe Gly Asp Lys Tyr
            210                 215                 220

Arg Asp Arg Tyr Asp Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Asp Arg Gly Tyr Asp Ser
            260                 265                 270

Arg Ile Gly Ser Gly Arg Arg Ala Phe Gly Ser Gly Tyr Arg Arg Asp
            275                 280                 285

Asp Tyr Arg Gly Gly Gly Asp Arg Tyr Glu Asp Arg Tyr Asp Arg
            290                 295                 300

Arg Asp Asp Arg Ser Trp Ser Ser Arg Asp Asp Tyr Ser Arg Asp Asp
305                 310                 315                 320

Tyr Arg Arg Asp Asp Arg Gly Pro Pro Gln Arg Pro Lys Leu Asn Leu
                325                 330                 335

Lys Pro Arg Ser Thr Pro Glu Glu Asp Ser Ser Ala Ser Thr Ser
            340                 345                 350

Gln Ser Thr Arg Ala Ala Ser Ile Phe Gly Gly Ala Lys Pro Val Asp
            355                 360                 365

Thr Ala Ala Arg Glu Arg Glu Val Glu Glu Arg Leu Gln Lys Glu Gln
            370                 375                 380

Glu Lys Leu Gln Arg Gln Trp Asn Glu Pro Lys Leu Glu Arg Arg Pro
385                 390                 395                 400

Arg Glu Arg His Pro Ser Trp Arg Ser Glu Glu Thr Gln Glu Arg Glu
                405                 410                 415

Arg Ser Arg Thr Gly Ser Glu Ser Ser Gln Thr Gly Thr Ser Thr Thr
            420                 425                 430

Ser Ser Arg Asn Ala Arg Arg Glu Ser Glu Lys Ser Leu Glu Asn
            435                 440                 445

Glu Thr Leu Asn Lys Glu Glu Asp Cys His Ser Pro Thr Ser Lys Pro
    450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
                485                 490                 495

Ser Ser Asp Thr Glu Gln Gln Ser Pro Thr Ser Gly Gly Lys Val
            500                 505                 510

Ala Pro Ala Gln Pro Ser Glu Glu Gly Pro Gly Arg Lys Asp Glu Asn
            515                 520                 525

Lys Val Asp Gly Met Asn Ala Pro Lys Gly Gln Thr Gly Asn Ser Ser
530                 535                 540

Arg Gly Pro Gly Asp Gly Gly Asn Arg Asp His Trp Lys Glu Ser Asp
545                 550                 555                 560

Arg Lys Asp Gly Lys Asp Gln Asp Ser Arg Ser Ala Pro Glu Pro
                565                 570                 575

Lys Lys Pro Glu Glu Asn Pro Ala Ser Lys Phe Ser Ser Ala Ser Lys
            580                 585                 590
```

```
Tyr Ala Ala Leu Ser Val Asp Gly Glu Asp Glu Asn Glu Gly Glu Asp
        595                 600                 605
Tyr Ala Glu
    610

<210> SEQ ID NO 10
<211> LENGTH: 1970
<212> TYPE: PRT
<213> ORGANISM: Homo sapiens

<400> SEQUENCE: 10

Met His Gly Gly Gly Pro Pro Ser Gly Asp Ser Ala Cys Pro Leu Arg
  1               5                  10                  15

Thr Ile Lys Arg Val Gln Phe Gly Val Leu Ser Pro Asp Glu Leu Lys
             20                  25                  30

Arg Met Ser Val Thr Glu Gly Gly Ile Lys Tyr Pro Glu Thr Thr Glu
         35                  40                  45

Gly Gly Arg Pro Lys Leu Gly Gly Leu Met Asp Pro Arg Gln Gly Val
     50                  55                  60

Ile Glu Arg Thr Gly Arg Cys Gln Thr Cys Ala Gly Asn Met Thr Glu
 65                  70                  75                  80

Cys Pro Gly His Phe Gly His Ile Glu Leu Ala Lys Pro Val Phe His
                 85                  90                  95

Val Gly Phe Leu Val Lys Thr Met Lys Val Leu Arg Cys Val Cys Phe
            100                 105                 110

Phe Cys Ser Lys Leu Leu Val Asp Ser Asn Asn Pro Lys Ile Lys Asp
        115                 120                 125

Ile Leu Ala Lys Ser Lys Gly Gln Pro Lys Lys Arg Leu Thr His Val
    130                 135                 140

Tyr Asp Leu Cys Lys Gly Lys Asn Ile Cys Glu Gly Gly Glu Glu Met
145                 150                 155                 160

Asp Asn Lys Phe Gly Val Glu Gln Pro Glu Gly Asp Glu Asp Leu Thr
                165                 170                 175

Lys Glu Lys Gly His Gly Gly Cys Gly Arg Tyr Gln Pro Arg Ile Arg
            180                 185                 190

Arg Ser Gly Leu Glu Leu Tyr Ala Glu Trp Lys His Val Asn Glu Asp
        195                 200                 205

Ser Gln Glu Lys Lys Ile Leu Leu Ser Pro Glu Arg Val His Glu Ile
    210                 215                 220

Phe Lys Arg Ile Ser Asp Glu Glu Cys Phe Val Leu Gly Met Glu Pro
225                 230                 235                 240

Arg Tyr Ala Arg Pro Glu Trp Met Ile Val Thr Val Leu Pro Val Pro
                245                 250                 255

Pro Leu Ser Val Arg Pro Ala Val Val Met Gln Gly Ser Ala Arg Asn
            260                 265                 270

Gln Asp Asp Leu Thr His Lys Leu Ala Asp Ile Val Lys Ile Asn Asn
        275                 280                 285

Gln Leu Arg Arg Asn Glu Gln Asn Gly Ala Ala Ala His Val Ile Ala
    290                 295                 300

Glu Asp Val Lys Leu Leu Gln Phe His Val Ala Thr Met Val Asp Asn
305                 310                 315                 320

Glu Leu Pro Gly Leu Pro Arg Ala Met Gln Lys Ser Gly Arg Pro Leu
                325                 330                 335

Lys Ser Leu Lys Gln Arg Leu Lys Gly Lys Glu Gly Arg Val Arg Gly
            340                 345                 350
```

-continued

```
Asn Leu Met Gly Lys Arg Val Asp Phe Ser Ala Arg Thr Val Ile Thr
            355                 360                 365
Pro Asp Pro Asn Leu Ser Ile Asp Gln Val Gly Val Pro Arg Ser Ile
    370                 375                 380
Ala Ala Asn Met Thr Phe Ala Glu Ile Val Thr Pro Phe Asn Ile Asp
385                 390                 395                 400
Arg Leu Gln Glu Leu Val Arg Arg Gly Asn Ser Gln Tyr Pro Gly Ala
                405                 410                 415
Lys Tyr Ile Ile Arg Asp Asn Gly Asp Arg Ile Asp Leu Arg Phe His
            420                 425                 430
Pro Lys Pro Ser Asp Leu His Leu Gln Thr Gly Tyr Lys Val Glu Arg
    435                 440                 445
His Met Cys Asp Gly Asp Ile Val Ile Phe Asn Arg Gln Pro Thr Leu
450                 455                 460
His Lys Met Ser Met Met Gly His Arg Val Arg Ile Leu Pro Trp Ser
465                 470                 475                 480
Thr Phe Arg Leu Asn Leu Ser Val Thr Thr Pro Tyr Asn Ala Asp Phe
            485                 490                 495
Asp Gly Asp Glu Met Asn Leu His Leu Pro Gln Ser Leu Glu Thr Arg
            500                 505                 510
Ala Glu Ile Gln Glu Leu Ala Met Val Pro Arg Met Ile Val Thr Pro
        515                 520                 525
Gln Ser Asn Arg Pro Val Met Gly Ile Val Gln Asp Thr Leu Thr Ala
    530                 535                 540
Val Arg Lys Phe Thr Lys Arg Asp Val Phe Leu Glu Arg Gly Glu Val
545                 550                 555                 560
Met Asn Leu Leu Met Phe Leu Ser Thr Trp Asp Gly Lys Val Pro Gln
                565                 570                 575
Pro Ala Ile Leu Lys Pro Arg Pro Leu Trp Thr Gly Lys Gln Ile Phe
            580                 585                 590
Ser Leu Ile Ile Pro Gly His Ile Asn Cys Ile Arg Thr His Ser Thr
            595                 600                 605
His Pro Asp Asp Glu Asp Ser Gly Pro Tyr Lys His Ile Ser Pro Gly
    610                 615                 620
Asp Thr Lys Val Val Glu Asn Gly Glu Leu Ile Met Gly Ile Leu
625                 630                 635                 640
Cys Lys Lys Ser Leu Gly Thr Ser Ala Gly Ser Leu Val His Ile Ser
                645                 650                 655
Tyr Leu Glu Met Gly His Asp Ile Thr Arg Leu Phe Tyr Ser Asn Ile
            660                 665                 670
Gln Thr Val Ile Asn Asn Trp Leu Leu Ile Glu Gly His Thr Ile Gly
        675                 680                 685
Ile Gly Asp Ser Ile Ala Asp Ser Lys Thr Tyr Gln Asp Ile Gln Asn
    690                 695                 700
Thr Ile Lys Lys Ala Lys Gln Asp Val Ile Glu Val Ile Glu Lys Ala
705                 710                 715                 720
His Asn Asn Glu Leu Glu Pro Thr Pro Gly Asn Thr Leu Arg Gln Thr
                725                 730                 735
Phe Glu Asn Gln Val Asn Arg Ile Leu Asn Asp Ala Arg Asp Lys Thr
            740                 745                 750
Gly Ser Ser Ala Gln Lys Ser Leu Ser Glu Tyr Asn Asn Phe Lys Ser
    755                 760                 765
```

```
Met Val Val Ser Gly Ala Lys Gly Lys Ile Asn Ile Ser Gln Val
770                 775                 780
Ile Ala Val Val Gly Gln Gln Asn Val Glu Gly Lys Arg Ile Pro Phe
785                 790                 795                 800
Gly Phe Lys His Arg Thr Leu Pro His Phe Ile Lys Asp Asp Tyr Gly
                805                 810                 815
Pro Glu Ser Arg Gly Phe Val Glu Asn Ser Tyr Leu Ala Gly Leu Thr
                820                 825                 830
Pro Thr Glu Phe Phe Phe His Ala Met Gly Gly Arg Glu Gly Leu Ile
                835                 840                 845
Asp Thr Ala Val Lys Thr Ala Glu Thr Gly Tyr Ile Gln Arg Arg Leu
                850                 855                 860
Ile Lys Ser Met Glu Ser Val Met Val Lys Tyr Asp Ala Thr Val Arg
865                 870                 875                 880
Asn Ser Ile Asn Gln Val Val Gln Leu Arg Tyr Gly Glu Asp Gly Leu
                885                 890                 895
Ala Gly Glu Ser Val Glu Phe Gln Asn Leu Ala Thr Leu Lys Pro Ser
                900                 905                 910
Asn Lys Ala Phe Glu Lys Lys Phe Arg Phe Asp Tyr Thr Asn Glu Arg
                915                 920                 925
Ala Leu Arg Arg Thr Leu Gln Glu Asp Leu Val Lys Asp Val Leu Ser
                930                 935                 940
Asn Ala His Ile Gln Asn Glu Leu Glu Arg Glu Phe Glu Arg Met Arg
945                 950                 955                 960
Glu Asp Arg Glu Val Leu Arg Val Ile Phe Pro Thr Gly Asp Ser Lys
                965                 970                 975
Val Val Leu Pro Cys Asn Leu Leu Arg Met Ile Trp Asn Ala Gln Lys
                980                 985                 990
Ile Phe His Ile Asn Pro Arg Leu Pro Ser Asp Leu His Pro Ile Lys
                995                 1000                1005
Val Val Glu Gly Val Lys Glu Leu Ser Lys Lys Leu Val Ile Val Asn
                1010                1015                1020
Gly Asp Asp Pro Leu Ser Arg Gln Ala Gln Glu Asn Ala Thr Leu Leu
1025                1030                1035                1040
Phe Asn Ile His Leu Arg Ser Thr Leu Cys Ser Arg Arg Met Ala Glu
                1045                1050                1055
Glu Phe Arg Leu Ser Gly Glu Ala Phe Asp Trp Leu Leu Gly Glu Ile
                1060                1065                1070
Glu Ser Lys Phe Asn Gln Ala Ile Ala His Pro Gly Glu Met Val Gly
                1075                1080                1085
Ala Leu Ala Ala Gln Ser Leu Gly Glu Pro Ala Thr Gln Met Thr Leu
                1090                1095                1100
Asn Thr Phe His Tyr Ala Gly Val Ser Ala Lys Asn Val Thr Leu Gly
1105                1110                1115                1120
Val Pro Arg Leu Lys Glu Leu Ile Asn Ile Ser Lys Lys Pro Lys Thr
                1125                1130                1135
Pro Ser Leu Thr Val Phe Leu Leu Gly Gln Ser Ala Arg Asp Ala Glu
                1140                1145                1150
Arg Ala Lys Asp Ile Leu Cys Arg Leu Glu His Thr Thr Leu Arg Lys
                1155                1160                1165
Val Thr Ala Asn Thr Ala Ile Tyr Tyr Asp Pro Asn Pro Gln Ser Thr
                1170                1175                1180
Val Val Ala Glu Asp Gln Glu Trp Val Asn Val Tyr Tyr Glu Met Pro
```

```
            1185                1190                1195                1200

Asp Phe Asp Val Ala Arg Ile Ser Pro Trp Leu Leu Arg Val Glu Leu
                1205                1210                1215

Asp Arg Lys His Met Thr Asp Arg Lys Leu Thr Met Glu Gln Ile Ala
                1220                1225                1230

Glu Lys Ile Asn Ala Gly Phe Gly Asp Asp Leu Asn Cys Ile Phe Asn
                1235                1240                1245

Asp Asp Asn Ala Glu Lys Leu Val Leu Arg Ile Arg Ile Met Asn Ser
                1250                1255                1260

Asp Glu Asn Lys Met Gln Glu Glu Glu Val Val Asp Lys Met Asp
1265                1270                1275                1280

Asp Asp Val Phe Leu Arg Cys Ile Glu Ser Asn Met Leu Thr Asp Met
                1285                1290                1295

Thr Leu Gln Gly Ile Glu Gln Ile Ser Lys Val Tyr Met His Leu Pro
                1300                1305                1310

Gln Thr Asp Asn Lys Lys Ile Ile Ile Thr Glu Asp Gly Glu Phe
                1315                1320                1325

Lys Ala Leu Gln Glu Trp Ile Leu Glu Thr Asp Gly Val Ser Leu Met
                1330                1335                1340

Arg Val Leu Ser Glu Lys Asp Val Asp Pro Val Arg Thr Thr Ser Asn
1345                1350                1355                1360

Asp Ile Val Glu Ile Phe Thr Val Leu Gly Ile Glu Ala Val Arg Lys
                1365                1370                1375

Ala Leu Glu Arg Glu Leu Tyr His Val Ile Ser Phe Asp Gly Ser Tyr
                1380                1385                1390

Val Asn Tyr Arg His Leu Ala Leu Leu Cys Asp Thr Met Thr Cys Arg
                1395                1400                1405

Gly His Leu Met Ala Ile Thr Arg His Gly Val Asn Arg Gln Asp Thr
                1410                1415                1420

Gly Pro Leu Met Lys Cys Ser Phe Glu Glu Thr Val Asp Val Leu Met
1425                1430                1435                1440

Glu Ala Ala Ala His Gly Glu Ser Asp Pro Met Lys Gly Val Ser Glu
                1445                1450                1455

Asn Ile Met Leu Gly Gln Leu Ala Pro Ala Gly Thr Gly Cys Phe Asp
                1460                1465                1470

Leu Leu Leu Asp Ala Glu Lys Cys Lys Tyr Gly Met Glu Ile Pro Thr
                1475                1480                1485

Asn Ile Pro Gly Leu Gly Ala Ala Gly Pro Thr Gly Met Phe Phe Gly
                1490                1495                1500

Ser Ala Pro Ser Pro Met Gly Gly Ile Ser Pro Ala Met Thr Pro Trp
1505                1510                1515                1520

Asn Gln Gly Ala Thr Pro Ala Tyr Gly Ala Trp Ser Pro Ser Val Gly
                1525                1530                1535

Ser Gly Met Thr Pro Gly Ala Ala Gly Phe Ser Pro Ser Ala Ala Ser
                1540                1545                1550

Asp Ala Ser Gly Phe Ser Pro Gly Tyr Ser Pro Ala Trp Ser Pro Thr
                1555                1560                1565

Pro Gly Ser Pro Gly Ser Pro Gly Pro Ser Ser Pro Tyr Ile Pro Ser
                1570                1575                1580

Pro Gly Gly Ala Met Ser Pro Ser Tyr Ser Pro Thr Ser Pro Ala Tyr
1585                1590                1595                1600

Glu Pro Arg Ser Pro Gly Gly Tyr Thr Pro Gln Ser Pro Ser Tyr Ser
                1605                1610                1615
```

-continued

```
Pro Thr Ser Pro Ser Tyr Ser Pro Thr Ser Pro Ser Tyr Ser Pro Thr
            1620                1625                1630

Ser Pro Asn Tyr Ser Pro Thr Ser Pro Ser Tyr Ser Pro Thr Ser Pro
            1635                1640                1645

Ser Tyr Ser Pro Thr Ser Pro Ser Tyr Ser Pro Thr Ser Pro Ser Tyr
            1650                1655                1660

Ser Pro Thr Ser Pro Ser Tyr Ser Pro Thr Ser Pro Ser Tyr Ser Pro
1665                1670                1675                1680

Thr Ser Pro Ser Tyr Ser Pro Thr Ser Pro Ser Tyr Ser Pro Thr Ser
            1685                1690                1695

Pro Ser Tyr Ser Pro Thr Ser Pro Ser Tyr Ser Pro Thr Ser Pro Ser
            1700                1705                1710

Tyr Ser Pro Thr Ser Pro Ser Tyr Ser Pro Thr Ser Pro Ser Tyr Ser
            1715                1720                1725

Pro Thr Ser Pro Ser Tyr Ser Pro Thr Ser Pro Ser Tyr Ser Pro Thr
            1730                1735                1740

Ser Pro Asn Tyr Ser Pro Thr Ser Pro Asn Tyr Thr Pro Thr Ser Pro
1745                1750                1755                1760

Ser Tyr Ser Pro Thr Ser Pro Ser Tyr Ser Pro Thr Ser Pro Asn Tyr
            1765                1770                1775

Thr Pro Thr Ser Pro Asn Tyr Ser Pro Thr Ser Pro Ser Tyr Ser Pro
            1780                1785                1790

Thr Ser Pro Ser Tyr Ser Pro Thr Ser Pro Ser Tyr Ser Pro Ser Ser
            1795                1800                1805

Pro Arg Tyr Thr Pro Gln Ser Pro Thr Tyr Thr Pro Ser Ser Pro Ser
            1810                1815                1820

Tyr Ser Pro Ser Ser Pro Ser Tyr Ser Pro Thr Ser Pro Lys Tyr Thr
1825                1830                1835                1840

Pro Thr Ser Pro Ser Tyr Ser Pro Ser Ser Pro Glu Tyr Thr Pro Thr
            1845                1850                1855

Ser Pro Lys Tyr Ser Pro Thr Ser Pro Lys Tyr Ser Pro Thr Ser Pro
            1860                1865                1870

Lys Tyr Ser Pro Thr Ser Pro Thr Tyr Ser Pro Thr Thr Pro Lys Tyr
            1875                1880                1885

Ser Pro Thr Ser Pro Thr Tyr Ser Pro Thr Ser Pro Val Tyr Thr Pro
            1890                1895                1900

Thr Ser Pro Lys Tyr Ser Pro Thr Ser Pro Thr Tyr Ser Pro Thr Ser
1905                1910                1915                1920

Pro Lys Tyr Ser Pro Thr Ser Pro Thr Tyr Ser Pro Thr Ser Pro Lys
            1925                1930                1935

Gly Ser Thr Tyr Ser Pro Thr Ser Pro Gly Tyr Ser Pro Thr Ser Pro
            1940                1945                1950

Thr Tyr Ser Leu Thr Ser Pro Ala Ile Ser Pro Asp Asp Ser Asp Glu
            1955                1960                1965

Glu Asn
    1970
```

PROTEIN MARKERS OF RESPONSIVENESS TO TYPE III RECEPTOR TYROSINE KINASE INHIBITORS

RELATED APPLICATIONS

This application claims priority to, and the benefit of, U.S. Ser. No. 60/788,172, filed Mar. 31, 2006, the disclosure of which is hereby incorporated herein in its entirety by reference.

JOINT RESEARCH AGREEMENT

This application describes and claims certain subject matter that was developed under a written joint research and development agreement between CELL SIGNALING TECHNOLOGY, INC., and OSI PHARMACEUTICALS, INC., having an effective date of Jul. 25, 2003, pertaining to markers of cancer drug resistance or responsiveness.

FIELD OF THE INVENTION

The invention relates generally to cancer, to protein markers of drug response, and to reagents for the characterization of cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the phosphorylation state, and thus the activity of, particular signaling proteins. Cancer is the leading cause of death in individuals under the age of 85. It is estimated that over 560,000 patients will die in 2006 from the disease in the United States alone. See "*Cancer Facts and Figures* 2005," American Cancer Society.

Many of the signaling defects underlying cancer involve aberrant expression and activity of kinases, including receptor tyrosine kinases. Among the tyrosine kinases implicated in cancer are the Type III Receptor Tyrosine Kinases (RTKs), a family of split kinase domain enzymes that includes c-Kit (Kit, Kinase Insert Domain), VEGF Receptor 2 (VEGFR-2, KDR), Platelet-Derived Growth Factor Receptor (PDGFR), Colony Stimulating Factor-1 Receptor (CSF-1R) and FMS-related Tyrosine Kinase (FLT3). Activating mutations in Kit cause over 90% of gastrointestinal stromal (GIS) tumors, and also induce mastocytosis. See Fletcher et al. *Lancet Oncol.* 11: 655-64 (2002). Kit defects have also been associated with some small cell lung tumors, and loss of expression is associated with melanoma. See Potti et al. *Annal. Oncol.* 14: 894-7, (2003) and Ohashi et al. *Melanoma Res* 6: 25-30 (1996). KDR is required for angiogenesis and is disregulated in a variety of solid tumors. See Neufeld et al. *FASEB* 13: 9-22 (1999). PDGFR mutations cause a minority of GIST tumors, and its fusion to other proteins leads to a variety of myeloproliferative disorders and cancers, including eosinophilic leukemia, chronic monomyelocytic leukemia, and gliomas. See Jones et al., *Cell Mol Life Sci* 61: 291-23 (2004).

Defects in CSF1R expression and/or activation have been found in acute myeloid leukemia and myelodysplastic syndrome (MDS). See, e.g. Casas et al., *Leuk. Lymphoma* 44: 1935-1941 (2003); Li et al., *Leukemia Res.* 26: 377-382 (2002). Elevated coexpression of CSF1R and its ligand, CSF1, have been correlated with invasiveness and poor prognosis of epithelial tumors including breast, ovarian and endometrial cancer. See Kacinski B M, *Ann. Med.* 27: 79-85 (1995). Activating point mutations in CSF1R have also been detected in AML and CMML. See Ridge et al., *Proc Natl Acad Sci USA* 87(4): 1377-80 (1990); Tobal et al., *Leukemia* 4(7): 486-89 (1990)).

Due to their causative role in a variety of cancers, Type III RTKs have increasingly become targets for the development of new small molecule inhibitors for the treatment of cancers driven by aberrant expression/activity of these RTKs. In particular, since it believed that many cancers have more than kinase driving the disease, multi-target inhibitors with activity against multiple Type III RTKs are currently being developed. For example, Amgen is developing AMG706, a compound with activity against PDGFR and Kit, as well as other kinases. Bayer and Onyx Pharmaceuticals have developed BAY 43-9006 (Nexavar® (sorafenib)), a compound also having activity against PDGFR and Kit, as well as other kinases. Millennium Pharmaceuticals is developing MLN518, an inhibitor of Type III RTKs including PDGFR and Kit. Novartis, Inc. is developing PKC412 and AMN107, two compounds with activity against PDGFR and Kit, as well as other kinases, and its approved small-molecule BRC-ABL inhibitor, Gleevec® (STI-571; Imatinib) also inhibits Kit and PDGFR. Pfizer, Inc.'s approved compound Sutent® (SU1 1248, Sunitinib Maleate) inhibits CSF-1R, PDGFR, and Kit, as well as other kinases. And, OSI Pharmaceuticals is developing two compounds, OSI-930 and OSI-817, having activity against c-Kit, as well as VEGFR.

Despite the ongoing development of such kinase-targeted therapeutics, it is now well recognized that certain subsets of patients will often be resistant to such drugs, despite having a cancer in which the targeted RTK is over-expressed or over-activated. The mechanisms of such resistance are often the presence of mutant forms of the targeted RTK that do not respond to the drug, and/or the presence of alternative signaling pathways that are driving the cancer and are not targeted by the drug.

For example, clinical results since the introduction of Gleevec® (Imatinib mesylate; STI-571), a small molecule targeted inhibitor of BCR-ABL fusion kinase approved for treatment of chronic myelogenous leukemia (and more recently, GIST), have shown that patients often develop resistance to the drug. See, e.g. Sawyers, *Science* 294(5548): 1834 (2001). The mechanism of resistance may vary from patient to patient, but is most often a result of mutant forms of the kinase that are not affected by the inhibitor.

Improved BCR-ABL kinase inhibitors are therefore now being developed that will target the mutant forms of BCR-ABL kinase. However, one particular mutation, T351I, remains resistant to even the new generation of BCR-ABL inhibitors. It is therefore important to identify as early as possible during the course of Gleevec® treatment if resistance starts to arise, and whether a patient having or developing resistance may be switched to other BCR-ABL inhibitors or combinations of them, to increased doses of Gleevec®, or to alternative treatments such as bone marrow transplantation in the case of T315I mutations. Therefore, the discovery of biomarkers to allow the accurate and early identification of patients resistant to Gleevec® will be paramount.

Similarly, there is an important and pressing need to identify biomarkers of resistance or responsiveness to the growing number of therapeutics that target Type III RTKs. These drugs are part of a new class of targeted agents designed to interfere with the signaling pathways and kinases, such as Kit and PDGFR, that drive the growth of tumor cells or support tumor growth through improved angiogenesis and oncogenic stromal signaling. The development of these drugs represents a significant advance over the conventional therapies for cancer, chemotherapy and radiation, which are plagued by well-known side effects and are often of limited effect since they fail to specifically target the underlying causes of the malignancies. Nonetheless, as the era of personalized medicine approaches, it will become ever more important to discover and define protein biomarkers that predict whether a given patient is likely to respond, or be resistant to, a particular therapeutic or combination of therapeutics, in order to timely select the most efficacious treatment.

Accordingly, there remains a need for the discovery of protein biomarkers of resistance or responsiveness to inhibitors of Type III RTKs, including Kit, KDR, PDGFR, and CSF-1R. The identification of such markers and development of diagnostic assays based on the same would greatly assist in optimally treating a given patient having a cancer driven in whole or in part by one or more Type III RTKs, as well as to monitor resistance to such inhibitors as it develops. These biomarkers would also greatly assist in improving the efficiency and accuracy of clinical trials of inhibitors of Type III RTKs, by helping select patients most likely to respond to the compounds and/or by reducing the risk of late-stage clinical failures.

SUMMARY OF THE INVENTION

The invention discloses ten protein markers, Heat Shock Protein-27 (HSP-27), Cortactin, Cdc25C (or phospho-Cdc25C (Ser216 or Thr48)), phospho-MAPKAPK-2 (Thr334), phospho-Cyclin E (Thr62), Stathmin, phospho-ATF2 (Thr69 or Thr71), phospho-Histone H3 (Thr3), phospho-EIF-4B (Ser422), and phospho-Rpb1 (Ser2 or Ser5), that are predictive of cancer resistance or responsiveness to targeted inhibitors of Type III Receptor Tyrosine Kinases (RTKs). Also provided are methods for obtaining information useful for identifying a cancer that is likely to be resistant or responsive to a Type III RTK-inhibiting therapeutic by determining the pattern of expression/activity of one or more of the disclosed protein markers in a biological sample from the cancer. Methods for identifying a compound that inhibits a Type III RTK inhibitor-resistant cancer by determining the effect of the compound on one or more of the disclosed marker proteins are also provided.

BRIEF DESCRIPTION OF THE DRAWINGS

FIG. 1—is a table describing the xenograft models used in the IHC analysis.

FIG. 2—is an unsupervised hierarchical correlation diagram (heat map) showing that the xenograft models resistant to OSI-930 cluster together.

FIG. 3—is a supervised hierarchical correlation diagram (heat map) showing that minimal signatures of 3 to 11 markers may be used to statistical predict resistance or responsiveness to OSI-930.

FIG. 4—is the amino acid sequence of human heat shock protein-27 (HSP-27) (SwissProt accession # PO4792) (SEQ ID NO: 1).

FIG. 5—is the amino acid sequence of human Cortactin protein (SwissProt accession # Q14247) (SEQ ID NO: 2).

FIG. 6—is the amino acid sequence of human cdc25C protein (SwissProt accession # P30307) (SEQ ID NO: 3).

FIG. 7—is the amino acid sequence of human MAP-KAPK-2 protein (SwissProt accession # P49137) (SEQ ID NO: 4).

FIG. 8—is the amino acid sequence of human Cyclin-E protein (SwissProt accession # P24864) (SEQ ID NO: 5).

FIG. 9—is the amino acid sequence of human stathmin protein (SwissProt accession # P16949) (SEQ ID NO: 6).

FIG. 10—is the amino acid sequence of human ATF-2 protein (SwissProt accession # P15336) (SEQ ID NO: 7).

FIG. 11—is the amino acid sequence of human Histone H3 protein (SwissProt accession # Q16695) (SEQ ID NO: 8).

FIG. 12—is the amino acid sequence of human EIF-4B protein (SwissProt accession # P23588) (SEQ ID NO: 9).

FIG. 13—is the amino acid sequence of human Rpb1 protein (SwissProt accession # P24928) (SEQ ID NO: 10).

DETAILED DESCRIPTION OF THE INVENTION

In accordance with the present invention, ten (10) protein markers that are correlated with cancer resistance or responsiveness to Type III Receptor Tyrosine Kinase (RTK) inhibitors have now been identified. Type III RTKs are a family of split kinase domain enzymes that includes c-Kit (Kit, Kinase Insert Domain), VEGF Receptor 2 (VEGFR-2, KDR), Platelet-Derived Growth Factor Receptor (PDGFR), Colony Stimulating Factor-1 Receptor (CSF-1R) and FMS-related Tyrosine Kinase (FLT3). Many targeted inhibitors of this family of kinases, including AMG706 (Amgen), BAY 43-9006 ((Nexavar®) (Bayer)), MLN518 (Millennium), and OSI-930 as well as OSI-817 (both OSI Pharmaceuticals), are in development for the treatment of various cancers.

The ten biomarkers and were identified by employing large scale immunohistochemistry (IHC) screening of 18 xenograft models (corresponding to a variety of human cancers), utilizing 200 phospho-specific and total antibodies to examine signaling activity, to determine correlated markers predictive of resistance or responsiveness to OSI-930, a compound with activity against Kit, PDGFR, and KDR. Automated imaging was employed to develop a correlation map with higher sensitivity and better quantitation than the traditional 0-3 manual rating system for pathology. Both compound-sensitive and compound-resistant tumor xenografts were examined. The screening and identification of these ten correlated resistance or responsiveness biomarkers is described in more detail in Example 1 below.

The screen identified many proteins correlated with resistance or responsiveness to OSI-930 in these xenografts models. The ten most highly correlated Type III RTK inhibitor resistance or responsiveness marker proteins, as disclosed herein, are: Heat Shock Protein-27 (HSP-27), Cortactin, Cdc25C (or phospho-Cdc25C (Ser216 or Thr48)), phospho-MAPKAPK-2 (Thr334), phospho-Cyclin E (Thr62), stathmin, phospho-ATF2 (Thr69 or Thr71), phospho-Histone H3 (Thr3), phospho-EIF-4B (Ser422), and phospho-Rpb1 (Ser2 or Ser5). The full sequences of these human proteins are publicly available in the SwissProt database and their Accession numbers are listed in the Brief Description of the Drawings and provided in FIGS. 2-11. All of these markers are phosphorylated at the particular threonine or serine sites indicated, except HSP-27, Cortactin, Cdc25C and Stathmin.

Although certain of the disclosed marker proteins, HSP-27, ATF2, cyclin E and stathmin have previously been associated with resistance to proteosome inhibitors or chemotherapeutic agents (see Chauhan et al. *Apoptosis* 9: 149-55 (2004); Ciocca et al., *Cell Stress Chaperones* 10: 86-103 (2005); Hayakawa et al., *JBC* 278: 20582-92 (2003); Smith et al., *Mol. Pharamcol.* 60: 885-93 (2001); and Balachandran et al. *Oncogene* 22: 8924-30 (2003)), their differential expression/activity in and correlation to Type III RTK inhibitor resistance and usefulness as markers of such resistance has not previously been described.

The discovery of the ten protein markers differentially expressed/activated between Type III RTK inhibitor resistant and responsive cancers enables the identification of cancers, tumors, and patients likely to be resistant or responsive to a Type III RTK-inhibiting therapeutic administered for the treatment of such cancer.

Accordingly, the invention provides, in part, a method for obtaining information useful for determining whether a cancer that is likely to be resistant or responsive to a Type III Receptor Tyrosine Kinase (RTK)-inhibiting therapeutic, the method comprising the step of examining a biological sample from the cancer for the expression and/or activation of one or more marker proteins selected from the group consisting of Heat Shock Protein-27 (HSP-27), Cortactin, Cdc25C (or phospho-Cdc25C (Ser216 or Thr48)), phospho-MAP-KAPK-2 (Thr334), phospho-Cyclin E (Thr62), stathmin, phospho-ATF2 (Thr69 or Thr71), phospho-Histone H3 (Thr3), phospho-EIF-4B (Ser422), and phospho-Rpb1 (Ser2 or Ser5) (see SEQ ID NOs: 1-10; FIGS. 4-13), wherein the pattern of expression and/or activity of said one or more marker proteins information useful in determining whether said cancer as likely to be resistant or responsive to a Type III RTK-inhibiting therapeutic.

In some preferred embodiments, the biological sample is a tumor sample, a blood sample, or a bone marrow sample. In another preferred embodiment, the Type III RTK-inhibiting therapeutic comprises OSI-930. In other preferred embodiments, the Type III RTK-inhibiting therapeutic comprises a therapeutic selected from the group consisting of AMG706, BAY 43-9006 (Nexavar® (sorafenib)), MLN518, PKC412, AMN107, Gleevec® (STI-571; Imatinib), Sutent® (SU11248, Sunitinib Maleate), and OSI-817. In yet another preferred embodiment, the cancer is selected from the group consisting of Small Cell Lung Cancer, Colorectal Cancer, Head and Neck Cancer, Ovarian Cancer, Melanoma, Renal Cell Carcinoma, Pancreatic Cancer and Non-Small Cell Lung Cancer.

In one preferred embodiment of the method, expression/activity of a single marker protein is examined. In another preferred embodiment two or more marker proteins are examined. While in still another preferred embodiment three or more marker proteins are examined. In one particularly preferred embodiment, the expression/activity of HSP-27 and two or more other marker proteins is examined. For example, in one particularly preferred embodiment, the expression/activity of HSP-27, phospho-ATF2 (Thr69/71), and at least one of Cdc25C and/or phospho-Cdc25C (Ser216 or Thr48) are examined. In another particularly preferred embodiment, the expression/activity of HSP-27 and phospho-ATF2 (Thr69/71) together with (i) at least one of cdc25C, phospho-cdc25C (Ser216 or Thr48), and/or phospho-MAPKAPK-2 (Thr334) and (ii) phospho-Cyclin-E (Thr62) are examined.

In still another particularly preferred embodiment, the expression/activity of the expression/activity of HSP-27, phospho-ATF2 (Thr69/71), and phospho-Cdc25C (Ser216 or Thr48) are examined. In another particularly preferred embodiment, the expression/activity of HSP-27, phospho-ATF2 (Thr69/71), Cortactin, phospho-Histone H3 (Thr3), phospho-EIF-4B (Ser422), phospho-Cyclin-E (Thr62), and phospho-Rpb1 (Ser2/5) together with (i) at least one of cdc25C, phospho-cdc25C (Ser216 or Thr48), and/or phospho-MAPKAPK-2 (Thr334) are examined.

In yet another preferred embodiment, expression/activity of five or more of the disclosed marker proteins is examined, while in still another preferred embodiment, expression activity of all ten of the disclosed marker proteins is examined.

In other preferred embodiments, marker-specific and/or phosphorylation-site specific antibodies, and AQUA peptides, are utilized to detect the expression and/or activity of the resistance or responsiveness markers. In some preferred embodiments, the method of the invention utilizes a whole-cell assay, such as immunohistochemistry (IHC), flow cytometry (FC), or immuno-fluorescence (IF).

The invention also provides a kit for the identification of a cancer that is likely to be resistant to a Type III RTK-inhibiting therapeutic for the treatment of said cancer, the kit comprising said kit comprising detectable reagents against three or more of the disclosed marker proteins. In a preferred embodiment of the kit, the detectable reagents comprise a marker protein-specific antibody or a heavy isotope-labeled peptide corresponding to a unique sequence on the marker protein. Antibodies and AQUA peptides useful in practicing the methods of the invention are described in detail in Sections A and B below.

Definitions.

As used herein, the following terms have the meanings indicated:

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "does not bind" with respect to an antibody's binding to one phospho-form of a sequence means does not substantially react with as compared to the antibody's binding to the other phospho-form of the sequence for which the antibody is specific.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Marker Protein" is used interchangeably with "biomarker" and "resistance or responsiveness marker" and means any of the ten Type III RTK-inhibitor resistance or responsiveness markers described and disclosed herein.

"Over-expressed" or "Over-activated" with respect to a marker protein in a biological sample means the expression and/or activity of the marker protein is significantly higher than in a suitable control sample.

"Protein" is used interchangeably with polypeptide, and includes protein fragments and domains as well as whole protein.

"Phosphoprotein" means a protein comprising at least one phosphorylated amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

"Type III RTK-Inhibitor" or "Type III RTK-inhibiting therapeutic" means any composition comprising at least one compound, chemical or biological, capable of inhibiting, directly or indirectly, a kinase that is a member of the Type III receptor tyrosine kinase family, including, but not limited to, Kit, KDR, PDGFR, and CSF-1R kinases.

All referenced cited above and below are hereby incorporated herein in their entirety. The further aspects and advantages of invention are described in detail below.

A. Antibodies and Cell Lines

Antibodies useful in the methods of the invention specifically bind to one of the Type III RTK-inhibitor resistance or responsiveness marker proteins disclosed herein. Phospho-specific antibodies useful in the methods of the invention bind a phosphorylated marker protein (e.g. phospho-Histone H3 (Thr3)) only when phosphorylated at the amino acid (serine or threonine) indicated and do not substantially bind to the non-phosphorylated versions of the proteins.

Antibodies useful in the practice of the invention include (a) monoclonal antibodies, (b) purified polyclonal antibodies, (c) antibodies as described in (a)-(b) above that bind equivalent and highly phosphorylation sites in other non-human species proteins (e.g. mouse, rat), as disclosed herein, and (d) fragments of (a)-(c) above that bind to the antigen (or more preferably the epitope) bound by the antibodies described above.

Such antibodies and antibody fragments that are within the scope of the present invention may be produced by a variety of techniques well known in the art, as further discussed below. Antibodies that bind to the phosphorylated proteins can be identified in accordance with known techniques.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.)

Polyclonal antibodies of the invention may be produced according to standard techniques by immunizing a suitable animal (e.g., rabbit, goat, etc.) with an antigen encompassing the desired epitope (e.g. a phosphorylation site) of the marker proteins disclosed herein, collecting immune serum from the animal, and separating the polyclonal antibodies from the immune serum, and purifying polyclonal antibodies having the desired specificity, in accordance with known procedures. The antigen may be a synthetic phosphopeptide antigen comprising the sequence surrounding and including the phosphorylation site, as described above, the antigen being selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)).

Monoclonal antibodies of the invention may be produced in a hybridoma cell line according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Alternatively, immortalized monoclonal antibody producing cell lines may be produced without fusion hybridomas, for example, by using transgenic spleen cells that are conditionally immortal. See, e.g. Pasqualini et al., *PNAS* 101(1): 257-259 (2004); Jat et al., U.S. Pat. No. 5,866,759 (Issued Feb. 2, 1999).

Monoclonal Fab fragments may also be produced in *Escherichia coli* by recombinant techniques known to those skilled in the art. See, e.g., W. Huse, *Science* 246:1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)).

Recombinant cells producing desired antibodies may also be employed, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Antibodies of the invention, whether polyclonal or monoclonal, may be screened for epitope- or phospho-specificity according to standard techniques. See, e.g. Czemik et al., *Methods in Enzymology,* 201: 264-283 (1991). For example, the antibodies may be screened against a peptide library by ELISA to ensure specificity for both the desired antigen and for reactivity only with the fusion form of the antigen. The antibodies may also be tested by Western blotting against cell preparations containing the marker proteins. Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity.

Phosphorylation-site specific antibodies may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the carcinoma-related signaling protein epitope for which the antibody of the invention is specific. In certain cases, polyclonal antisera may exhibit some undesirable general cross-reactivity to phosphotyrosine itself, which may be removed by further purification of antisera, e.g. over a phosphotyramine column.

Antibodies useful in the methods of the invention may also be advantageously conjugated to fluorescent dyes (e.g. Alexa 488, PE) for use in multi-parametric analyses along with other signal transduction and/or cell marker antibodies. They may also be desirably employed in a kit for the identification of a cancer that is likely to be resistant to a Type III RTK-inhibiting therapeutic, as further described herein.

The antibodies may be further characterized via immunohistochemical (IHC) staining using normal and diseased tissues to examine the presence of these markers in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies against many if not most of the ten disclosed biomarkers are also commercially available. For example, Cell Signaling Technology, Inc., sells specific antibodies for phospho-Cyclin E (Thr62), Cortactin, and phospho-EIF-4B (Ser422) (Catalogue Nos. 4136, 3502, and 3591, respectively).

Included in the practice of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies useful in practicing the invention specifically bind to human marker proteins, but are not limited only to binding the human species, per se. The invention includes antibodies that may also bind conserved and highly homologous or identical sites in other species (e.g. mouse, rat, monkey, yeast). Highly homologous or identical sites conserved in other species can readily be identified by standard sequence comparisons, such as using BLAST, with the human marker protein sequences referenced herein (see FIGS. 2-11).

B. Heavy-Isotope Labeled Peptides (AQUA Peptides).

Also useful in practicing the methods of the invention are heavy-isotope labeled peptides for the absolute quantification of the resistance or responsiveness marker proteins disclosed herein. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. A newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2$H, $^{13}$C, $^{15}$N, $^{17}$O, $^{18}$O, or $^{34}$S, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry (MS$^n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and MS$^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or MS$^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may be produced and utilized for any of the ten Type III RTK inhibitor resistance or responsiveness marker proteins disclosed herein. Peptide standards for a given phosphorylation site (e.g. the tyrosine Thr3 site in Histone H3) may be produced for both the phosphorylated and non-phosphorylated forms of the site (see SEQ ID NO: 8)) and such standards employed in the AQUA methodology to detect and quantify both forms of such phosphorylation site in a biological sample. Similarly, an AQUA peptide may be constructed or a unique sequence within a non-phosphorylated marker protein (e.g. HSP-27, Cortactin) (see SEQ ID NOs: 1 and 2) and employed in the methods of the invention.

AQUA peptides (as well as antibodies) of the invention may also be employed within a kit that comprises one or multiple AQUA peptide(s) described herein (for the quantification of a resistance or responsiveness marker protein). Such reagent is preferably provided in a detectable form. Optionally, a second detecting reagent conjugated to a detectable group may be employed. For example, a kit may include AQUA peptides for both the phosphorylated and non-phosphorylated form of a phosphorylation site within a marker protein disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

C. Detection Methods & Compound Screening.

The Type III RTK-inhibitor resistance or responsiveness markers presently disclosed enable powerful and previously unavailable methods for the rapid and simple detection of a cancer likely to resistant such inhibitor for the treatment of a cancer. The methods disclosed herein may be employed with any biological sample potentially containing, or suspected of containing, cells from a cancer that may be resistant to a Type III RTK inhibitor. Biological samples taken from human subjects for use in the methods disclosed herein are generally tumor samples, such as biopsy samples or fine needle aspirates, or biological fluids such as serum, blood plasma, or bone marrow, and may comprise whole cells or a cell lysate, whether or not purified. In a preferred embodiment, the biological sample comprises whole cells.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ or tissue of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36(3): 416-22 (1992))

In still another preferred embodiment, the biological sample comprises cells obtained from a NSCLC pleural effusion. Pleural effusions (liquid that forms outside the lung in the thoracic cavity and which contains cancerous cells) are known to form in many patients with advanced NSCLC, and the presence of such effusion is predictive of a poor outcome and short survival time. See Mott et al., *Chest* 119: 317-318 (2001). Effective and prompt treatment is therefore particularly critical in such cases. Standard techniques for obtaining pleural effusion samples have been described and are well known in the art (see Sahn *Clin Chest Med.* 3(2): 443-52 (1982)). Circulating cells may also be obtained from serum using tumor markers, cytokeratin protein markers or other methods of negative selection as described (see Ma et al. *Anticancer Res.* 23(1A): 49-62 (2003)).

Cellular extracts of the foregoing biological samples may be prepared, either crude or partially (or entirely) purified, in accordance with standard techniques, and used in the methods of the invention. Alternatively, biological samples comprising whole cells may be utilized in preferred assay formats such as immunohistochemistry (IHC), flow cytometry (FC), and immunofluorescence (IF), as further described in section D below. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In assessing biomarker expression in a biological sample comprising cells from a mammalian tumor, a control sample representing the background in vivo expression and/or activation of these markers may desirably be employed for comparative purposes. Ideally, the control sample comprises cells from a cancer that is representative of the subset of cancers in which these resistance or responsiveness markers are not expressed (i.e. from the responsive subset of patients). Comparing the level of expressed and/or active marker proteins in control sample versus the test biological sample thus identifies whether these marker proteins are over-expressed and/or over-activated.

In part, the invention provides a method for obtaining information useful for determining whether a mammalian cancer is likely to be resistant or responsive to a Type III Receptor Tyrosine Kinase (RTK)-inhibiting therapeutic for the treatment of said cancer, said method comprising the step of examining a biological sample from said cancer for the expression and/or activity of one or more marker proteins selected from the group consisting of:

(i) Heat Shock Protein-27 (HSP-27) (SEQ ID NO: 1),
(ii) Cortactin (SEQ ID NO: 2)
(iii) Cdc25C (or phospho-Cdc25C (Ser216 or Thr48) (SEQ ID NO: 3),
(iv) phospho-MAPKAPK-2 (Thr334) (SEQ ID NO: 4),
(v) phospho-Cyclin E (Thr62) (SEQ ID NO: 5),
(vi) stathmin (SEQ ID NO: 6),
(vii) phospho-ATF2 (Thr69 or Thr71) (SEQ ID NO: 7),
(viii) phospho-Histone H3 (Thr3) (SEQ ID NO: 8),
(ix) phospho-EIF-4B (Ser422) (SEQ ID NO: 9), and
(x) phospho-Rpb1 (Ser2 or Ser5) (SEQ ID NO: 10)

wherein, the pattern of expression and/or activity of said one or more marker proteins provides information useful in determining whether said cancer is likely to be resistant or responsive to a Type III RTK-inhibiting therapeutic.

In one preferred embodiment of the method, increased expression/activity of HSP-27, as compared to a control, identifies said cancer as likely to be resistant to said therapeutic, and decreased expression/activity of HSP-27, as compared to a control, identifies said cancer as likely to be responsive to said therapeutic. In another preferred embodiment, increased expression/activity of Cortactin, as compared to a control, identifies said cancer as likely to be resistant to said therapeutic, and decreased expression/activity of Cortactin, as compared to a control, identifies said cancer as likely to be responsive to said therapeutic.

In yet other preferred embodiments of the method, decreased expression/activity of any of phospho-ATF2 (Thr69/71), phospho-Histone H3 (Thr3), phospho-EIF-4B (Ser422), phospho-Rpb1 (Ser2/5), phospho-Cyclin-E (Thr62), cdc25C, phospho-cdc25C (Ser216 or Thr48), or phospho-MAPKAPK-2 (Thr334), as compared to a control, identifies said cancer as likely to be resistant to said therapeutic, and increased expression/activity of any of phospho-ATF2 (Thr69/71), phospho-Histone H3 (Thr3), phospho-EIF-4B (Ser422), phospho-Rpb1 (Ser2/5), phospho-Cyclin-E (Thr62), cdc25C, phospho-cdc25C (Ser216 or Thr48), or phospho-MAPKAPK-2 (Thr334), as compared to a control, identifies said cancer as likely to be responsive to said therapeutic.

In some preferred embodiments, the method employs one or more phospho-specific antibodies and/or AQUA peptides to detect the expression and/or activity of one or more of the above resistance or responsiveness marker proteins.

The method may be employed with a biological sample prior to contact with at least one Type III RTK inhibitor or is obtained from a cancer subject treated with such inhibitor. Accordingly, classification of marker protein activity and/or expression prior to contact of a biological sample with a test compound, such as a PDGFR inhibitor, may be examined to predict the effect of such compound. Accordingly, in one embodiment, the invention provides a method for identifying a compound that inhibits a cancer that is resistant to a Type III RTK-inhibiting therapeutic, said method comprising the steps of:

(a) contacting a biological sample from said cancer with said compound; and (b) determining the effect of said compound on the expression and/or activity of one or more marker proteins selected from the group consisting of:

(i) Heat Shock Protein-27 (HSP-27) (SEQ ID NO: 1),
(ii) Cortactin (SEQ ID NO: 2)
(iii) Cdc25C (or phospho-Cdc25C (Ser216 or Thr48) (SEQ ID NO: 3),
(iv) phospho-MAPKAPK-2 (Thr334) (SEQ ID NO: 4),
(v) phospho-Cyclin E (Thr62) (SEQ ID NO: 5),
(vi) phospho-Strathmin (SEQ ID NO: 6),
(vii) phospho-ATF2 (Thr69 or Thr71) (SEQ ID NO: 7),
(viii) phospho-Histone H3 (Thr3) (SEQ ID NO: 8),
(ix) phospho-EIF-4B (Ser422) (SEQ ID NO: 9), and
(x) phospho-Rpb1 (Ser2 or Ser5) (SEQ ID NO: 10), wherein, a decrease in the expression and/or activity of said one or more marker proteins following contact with said compound identifies said compound as inhibiting a cancer as likely to be resistant to a Type III RTK-inhibiting therapeutic.

Exemplary inhibitors of Type III RTKs include OSI-930, as well as AMG706, BAY 43-9006 (Nexavar® (sorafenib)), MLN518, PKC412, AMN107, Gleevec® (STI-571; Imatinib), Sutent® (SU11248, Sunitinib Maleate), and OSI-817, or their analogues. Inhibitory compounds may be targeted inhibitors that modulate the kinase activity of a Type III RTK, or may be upstream expression inhibitors, such as siRNA or anti-sense inhibitors. Such compound may, for example, directly inhibit kinase activity, or may indirectly inhibit its activity by, e.g., inhibiting another kinase that phosphorylates and thus activates the Type III RTK Biological samples may be obtained from a subject having, or at risk of having, a disease or condition involving Type III RTK expression or activity (e.g., SLCL or Ovarian cancer). For example, samples may be analyzed to monitor subjects who have been previously diagnosed as having a cancer, to screen subjects who have not been previously diagnosed as having cancer, or to monitor the desirability or efficacy of therapeutics targeted at a given Type III RTK active in said cancer.

In some preferred embodiments, the expression and/or activity of one or more of the ten resistance or responsiveness marker proteins disclosed herein is detected with a marker-specific antibody. Conditions suitable for the formation of antibody-antigen complexes are well known in the art (see part (D) below and references cited therein). It will be understood that more than one antibody may be used in the practice of the above-described methods.

The methods described above are applicable to examining tissues or biological samples from any cancer involving or characterized by the activity or expression of one or more Type III RTKs, in which the presence of the resistance or responsiveness markers disclosed herein has predictive value as to the response of the disease to actual or potential therapy. The methods are applicable, for example, where samples are taken from a subject previously diagnosed as having a cancer, such as SCLC, and under consideration for a Type III RTK-inhibitor, such as OSI-930, for treatment of the disease, and the method is employed to help assess early the likelihood of resistance or responsiveness to the targeted inhibitor.

Such diagnostic assay may be carried out prior to preliminary blood evaluation or surgical surveillance procedures. Such a diagnostic assay may be advantageously employed to identify patients with expression/activity of Type III RTKs likely to be resistant to targeted inhibitors against such kinases, or who relapse on a given anti-Type III RTK treatment, but would be likely to respond to other therapeutics. Such a selection of patients would be useful in the clinical evaluation of efficacy of future Type III RTK-inhibiting therapeutics as well as in the future prescription of such novel drugs to patients.

D. Immunoassay Formats & Kits

Assays carried out in accordance with methods of the present invention may be homogeneous assays or heterogeneous assays. In a homogeneous assay the immunological reaction usually involves a phosphospecific antibody of the invention as a reagent, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phospho-specific reagent, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110.

The concentration of detectable reagent should be sufficient such that the binding of mutant BCR-ABL is detectable compared to background.

The marker-specific antibodies described herein may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Reagents provided by the invention for the specific detection and/or quantification of one of the ten resistance or responsiveness marker proteins disclosed herein may be advantageously employed in whole-cell assays to detect the presence of such markers in a biological sample from a CML patient. Presence of the markers may be detected using total protein or peptide-specific reagents. Certain preferred whole-cell assays are described below.

Marker-specific antibodies of the invention may be advantageously employed in a flow cytometry (FC) assay to determine the presence of Type III RTK inhibitor-resistance or responsiveness markers in patients before, during, and after treatment with a drug targeted at inhibiting Type III RTK activity. For example, bone marrow cells or biopsy samples from patients may be analyzed by flow cytometry for Type III RTK expression, as well as for the protein markers disclosed herein. In this manner, the presence of a resistant cancer may be specifically characterized, using this clinically suitable assay format. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 2% paraformaldehyde for 10 minutes at 37° C. followed by permeabilization in 90% methanol for 30 minutes on ice. Cells may then be stained with the primary BCR-ABL antibody (or phosphoprotein marker antibody), washed and labeled with a fluorescent-labeled secondary antibody. The cells would then be analyzed on a flow cytometer (e.g. a Beckman Coulter FC500) according to the specific protocols of the instrument used. Such an analysis would identify the presence of the phosphorylated marker proteins of this invention in a cell of interest and reveal the drug response on the targeted BCR-ABL kinase.

Immunohistochemical (IHC) staining may be also employed to determine the expression and/or activation status of one or more of the resistance or responsiveness marker proteins in a biological sample from a cancer patient before, during, and after treatment with a Type III RTK inhibitor, such as OSI-930, or its analogues. IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. bone marrow from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-marker protein antibody (i.e. against any of the ten resistance or responsiveness marker proteins/sites disclosed herein) and secondary antibody; and finally detecting using ABC avidin/biotin method according to manufacturer's instructions.

Immunofluorescence (IF) assays may be also employed to determine the expression and/or activation status of one or more of the ten resistance or responsiveness marker proteins in a biological sample from a cancer before, during, and after treatment with a Type III RTK-inhibiting therapeutic. IF may be carried out according to well-known techniques. See, e.g., J. M. polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against the marker protein(s) followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa 488, PE), or other labels, such as quantum dots, for use in multi-parametric analyses along with other signal transduction (EGFR, phospho-AKT, phospho-Erk 1/2) and/or cell marker (cytokeratin) antibodies, as described earlier.

Kits for carrying out the methods disclosed above are also provided by the invention. Such kits advantageously comprise one or more (and most preferably three or more) detectable reagents suitable for assaying the marker proteins disclosed herein. Such detectable reagents may preferably be antibodies or AQUA peptides, as described above, either alone or in combination with reagents for the detection of proteins other than the ten resistance or responsiveness marker proteins.

The kits may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

E. Type III RTK-Inhibiting Therapeutics.

A Type III RTK-inhibiting therapeutic may be any composition comprising at least one compound, biological or chemical, which inhibits, directly or indirectly, the expression and/or activity of one or more Type III RTKs in vivo, including the exemplary classes of compounds described below. Such compounds include therapeutics that act directly on the Type III RTK itself, or on proteins or molecules that modify the activity of Type III RTK, or that act indirectly by inhibiting the expression of Type III RTK. Such compositions include compositions that comprise only a single Type III RTK-inhibiting compound, as well as compositions comprising multiple therapeutics (including those against other RTKs), which may also include a non-specific therapeutic agent like a chemotherapeutic agent or general transcription inhibitor. The inhibitor may have activity against only a single Type III RTK (e.g. PDGFR), or may have activity against multiple Type III RTKs (e.g. Kit, KDR, and PDGFR).

Small-Molecule Inhibitors.

In some preferred embodiments, a Type III RTK-inhibiting therapeutic for which the disclosed methods are useful is a targeted, small molecule inhibitor, such as OSI-930, and its analogues. As presently shown (see Example 1), screening of 200 signaling proteins in mice harboring a variety of human cancer xenografts both resistant and responsive to OSI-903, identified the ten disclosed biomarkers as most highly correlated to (and predictive of) resistance or responsiveness to OSI-930. OSI-930 is a small molecule targeted inhibitor of Kit, KDR, and PDGFR, which specifically binds to and blocks the ATP binding site, thereby preventing phosphorylation and activation of this enzyme. See Garton et al. *Cancer Res.* 66: 1015-24.

Other preferred small-molecule inhibitors of Type III RTKs are known to those of skill in the art. For example, Amgen is developing AMG706, a compound with activity against PDGFR and Kit, as well as other kinases. Bayer and Onyx Pharmaceuticals have developed BAY 43-9006 (Nexavar® (sorafenib)), a compound also having activity against PDGFR and Kit, as well as other kinases. Millennium Pharmaceuticals is developing MLN518, an inhibitor of Type III RTKs including PDGFR and Kit. Novartis, Inc. is developing PKC412 and AMN107, two compounds with activity against PDGFR and Kit, as well as other kinases, and its approved small-molecule BRC-ABL inhibitor, Gleevec® (STI-571; Imatinib) also inhibits Kit and PDGFR. Pfizer, Inc.'s approved compound Sutent® (SU11248, Sunitinib Maleate) inhibits CSF-1R, PDGFR, and Kit, as well as other kinases. And, OSI Pharmaceuticals is developing two compounds, OSI-930 and OSI-817, having activity against c-Kit, as well as VEGFR. These compounds are under clinical investigation and their PDGFRα-specific inhibitory properties have been described. See, e.g., Garton et al., supra.

Other classes of Type III RTK-inhibiting therapeutics for which the methods of the invention may advantageously be employed are briefly described below.

Antibody Inhibitors.

Targeted antibodies are those that specifically bind to critical catalytic or binding sites or domains required for kinase activity, and inhibit the kinase by blocking access of substrates or secondary molecules and/or preventing the enzyme from adopting a conformation necessary for its activity. The production, screening, and therapeutic use of humanized target-specific antibodies have been well described. See Merluzzi et al., *Adv Clin Path.* 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

Indirect Inhibitors.

Indirect inhibitors are compounds that indirectly inhibit a Type III RTK activity by inhibiting the activity of proteins or molecules other than the kinase itself. Such inhibiting therapeutics may be targeted inhibitors that modulate the activity of key regulatory kinases that phosphorylate or de-phosphorylate (and hence activate or deactivate) the target kinase itself. As with other receptor tyrosine kinases, Type III RTKs regulate downstream signaling through a network of adaptor proteins and downstream kinases. As a result, induction of cell growth and survival by Type III RTK kinase activity may be inhibited by targeting these interacting or downstream proteins. Drugs currently in development that exemplify this class include AKT inhibitors (RX-0201) and mTOR inhibitors (rapamycin and its analogs such as CC1-779, Rapamune and RAD001). Indirect inhibitors include compound that inhibit the binding of an activating molecule (e.g. the platelet-derived growth factor (PDGF) A or B), necessary for the target kinase (e.g. PDGFR) to adopt its active conformation. For example, the production and use of anti-PDGF antibodies has been described. See U.S. Patent Publication No. 20030219839, "Anti-PDGF Antibodies and Methods for Producing Engineered Antibodies," Bowdish et al.

Anti-Sense and/or Transcription Inhibitors.

Anti-sense and/or transcription inhibiting compounds are those that inhibit Type III RTK activity by blocking transcription of the gene encoding the target kinase. Fore example, the inhibition of various receptor kinases, including VEGFR, EGFR, and IGFR, and FGFR, by antisense therapeutics for the treatment of cancer has been described. See, e.g., U.S. Pat. Nos. 6,734,017; 6,710,174, 6,617,162; 6,340,674; 5,783,683; 5,610,288. Antisense oligonucleotides are designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM.* pp. 40-46 (1990); Van Der Krol et al., *BioTechniques* 6(10): 958-976 (1988); Skorski et al., *Proc. Natl. Acad. Sci. USA* (1994) 91: 4504-4508.

Small Interfering RNA.

Small interfering RNA molecule (siRNA) compositions, which inhibit translation, and hence activity, of target kinases through the process of RNA interference, may also be used to inhibit Type III RTK expression and/or activity. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, "Composition and Method for Inhibiting Expression of a Target Gene," Feb. 26, 2004, Kreutzer et al.; U.S. Patent Publication No. 20020086356, "RNA Sequence-Specific Mediators of RNA Interference," Jun. 12, 2003, Tuschl et al.; U.S. Patent Publication 20040229266, "RNA Interference Mediating Small RNA Molecules," Nov. 18, 2004, Tuschl et al.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g. Promega, Inc. Dharmacon, Inc. Detailed technical manuals on the design, construction, and use of dsRNA for RNAi are available. See, e.g. Dharmacon's "RNAi Technical Reference & Application Guide"; Promega's "RNAi: A Guide to Gene Silencing." The inhibition of receptor tyrosine kinases, such as VEGFR and EGFR using siRNA inhibitors has recently been described. See U.S. Patent Publication No. 20040209832, Oct. 21, 2004, McSwiggen et al.; U.S. Patent Publication No. 20030170891, Sep. 11, 2003, McSwiggen; U.S. Patent Publication No. 20040175703, Sep. 9, 2004, Kreutzer et al.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Identification of Protein Markers Correlated with Resistance or Responsiveness to a Type III RTK Inhibitor (OSI-930) in Human Tumor Xenografts In order to identify predictive biomarkers for the type III RTK inhibitor OSI-930, IHC analysis of a set of xenograft models that have varying responses to the drug was conducted with a large set of carefully validated antibodies (200 total and phospho-antibodies). The approach was improved by the use of an automated imaging method that was more sensitive and quantitative than the traditional 0-3 scoring system of IHC results.

The cell lines used in the xenografts were from a variety of cancer types (18 models total—see FIG. 1). Five of these cell line models were resistant to the drug as shown by growth curves of the xenograrft tumor mass (data not shown) while the other seven were sensitive to the drug and showed significant inhibition of tumor growth. All xenograft samples were analyzed by IHC and given a score by the imaging program based upon a grey scale value reflecting staining intensity in the defined tumor area. All 200 antibodies were obtained from Cell Signaling Technology, Inc. (Danvers, Mass.), and were directed to signaling molecules in a variety of different signaling pathways.

The IHC results from all 200 antibodies were entering into a clustering program (the TIGR MeV program) that normalized the data and produced heat maps that organized the results into groups based upon similarity (FIG. 2). The results supported the biological relevance of the analysis; i.e., proteins from similar pathways and processes clustered into groups as did xenograft models from a few of the cancer types (small cell lung cancer for example). Most significantly, the resistant cell models clustered into one group. This cluster allows one to identify minimum signatures of resistance or responsiveness.

Further supervised cluster analysis isolated signatures or combinations of up to 11 protein markers (FIG. 3), Heat Shock Protein-27 (HSP-27), Cortactin, Cdc25C (or phospho-Cdc25C (Ser216 or Thr48)), phospho-MAPKAPK-2 (Thr334), phospho-Cyclin E (Thr62), stathmin, phospho-ATF2 (Thr69 or Thr71), phospho-Histone H3 (Thr3), phospho-EIF-4B (Ser422), and phospho-Rpb1 (Ser2 or Ser5), that best statistically predict resistance or responsiveness to OSI-930. The eleven markers were selected as those with the highest p-values resulting from individual t-test. The combination of 11 markers gives the highest level of confidence in predicting resistance or responsiveness. Reducing the number of markers also reduced the confidence of the prediction, although the predictions were still statistically significant at the 0.01 confidence level, for individual markers as well as collections of three, four, and eight markers.

The proteins that were identified suggest a novel profile of resistance or responsiveness based upon cellular stress, because Type III RTK inhibitors also interfere with angiogenesis and stromal support for tumor cells.

EXAMPLE 2

IHC Identification of Mammalian Tumors Likely to be Resistant to a Type III RTK Inhibitor (OSI-930)

The success of therapeutics in medicine and especially in a complex disease such as cancer depends on the correct diagnosis choice of patients treated with the drug. This process requires knowledge of the specific patient markers that can be used to predict how the patient will respond to a given drug or class of drugs that share a common mechanism of action.

A mammalian tumor likely to be resistant to OSI-830 may be identified as follows. A diseased tissues sample is removed from the patient prior to treatment and analyzed by IHC analysis to characterize the protein expression levels or protein phosphorylation levels for up to 11 of the predictive markers described herein. The patient sample may consist of a tumor resection, tumor biopsy, tumor needle biopsy, fine needle aspirant, or other means of isolating cancerous cells for the patient. The samples may be analyzed by conventional IHC analysis followed by either manual scoring (0-3 scale based upon staining intensity and number of cells staining) or automated scoring based upon computer methods to determine staining intensity over a designated area.

The use of all 11 markers will give the most predictive power although the use of 3 markers will still be desirably predictive of response to the drug. The results of the IHC analysis may than be used to determine if the patient is likely to be resistant to OSI-930 or another drug that has a similar mechanism of action or shares target type III RTK targets. Patients that are found to have a tumor signature similar to the resistant signature identified herein (high HSP27, low phospho-ATF2 and low phospho-CDC25C levels) are very likely to be resistant to the drug are will benefit by being treated with an alternative therapy. Likewise, patients that do not have the signature (low HSP27, high phospho-ATF2 and high phospho-CDC25C levels) are likely to respond to the drug.

What is claimed is:

1. A method for determining whether a mammalian cancer is likely to be resistant or responsive to OSI-930 for the treatment of said cancer, said method comprising the step(s) of:

(a) examining a biological sample from said cancer for the expression and/or activity of one or more marker proteins selected from the group consisting of:
(i) Heat Shock Protein-27 (HSP-27) (SEQ ID NO: 1),
(ii) Cortactin (SEQ ID NO: 2)

(iii) Cdc25C (SEQ ID NO: 3),
(iv) phospho-Cdc25C (Ser216) (SEQ ID NO: 3),
(v) phospho-Cdc25C (Thr48) (SEQ ID NO: 3),
(vi) phospho-MAPKAPK-2 (Thr334) (SEQ ID NO: 4),
(vii) phospho-Cyclin E (Thr62) (SEQ ID NO: 5),
(viii) Stathmin (SEQ ID NO: 6),
(ix) phospho-ATF2 (Thr69) (SEQ ID NO: 7),
(x) phospho-ATF2 (Thr71) (SEQ ID NO:7),
(xi) phospho-Histone H3 (Thr3) (SEQ ID NO: 8),
(xii) phospho-EIF-4B (Ser422) (SEQ ID NO: 9),
(xiii) phospho-Rpb1 (Ser2) (SEQ ID NO: 10); and
(xiv) phospho-Rpb1 (Ser5) (SEQ ID NO: 10);

(b) identifying said cancer as being resistant to OSI-930 where there is decreased expression or activity of any of phospho-ATF2 (Thr69), phospho-ATF2 (Thr71), phospho-Histone H3 (Thr3), phospho-EIF-4B (Sr422), phospho-Rpb1 (Ser2), phospho-Rpb1 (Ser5), phospho-Cyclin-E (Thr62), cdc25C, phospho-cdc25C (Ser216), phospho-cdc25C (Thr48), or phospho-MAPKAPK-2 (Thr334) or increased expression or activity of HSP-27, Cortactin, or Stathmin relative to the same biomarker's expression or activity level in cancer that is responsive to OSI-930; or (c) identifying said cancer as being responsive to OSI-930 where there is increased expression or activity of any one of phospho-ATF2 (Thr69), phospho-ATF2 (Thr71), phospho-Histone H3 (Thr3), phospho-EIF-4B (Sr422), phospho-Rpb1 (Ser2), phospho-Rpb1 (Ser5), phospho-Cyclin-E (Thr62), cdc25C, phospho-cdc25C (Ser216), phospho-cdc25C (Thr48), or phospho-MAPKAPK-2 (Thr334) or decreased expression or activity of HSP-27, Cortactin, or Stathmin relative to the same biomarker's expression or activity level in cancer that is resistant to OSI-930.

2. The method of claim 1, wherein the expression and/or activity of two or more of said marker proteins, including HSP-27, is examined.

3. The method of claim 1, wherein the expression and/or activity of three or more of said marker proteins, including HSP-27, is examined.

4. The method of claim 3, wherein said three or more marker proteins comprise HSP-27, phospho-ATF2 (Thr69), phospho-ATF2 (Thr71), and at least one of Cdc25C, phospho-Cdc25C (Ser216), and/or phospho-Cdc25C (Thr48).

5. The method of claim 1, wherein the expression and/or activity of four or more of said marker proteins, including HSP-27, is examined.

6. The method of claim 5, wherein said four or more marker proteins comprise HSP-27, phospho-ATF2 (Thr69), phospho-ATF2 (Thr71), and phospho-Cyclin-E (Thr62) together with at least one of cdc25C, phospho-cdc25C (Ser216), phospho-cdc25C (Thr48), and/or phospho-MAPKAPK-2 (Thr334).

7. The method of claim 1, wherein the expression and/or activity of five or more of said marker proteins, including HSP-27, is examined.

8. The method of claim 1, wherein the expression and/or activity of eight or more of said marker proteins, including HSP-27, is examined.

9. The method of claim 8, wherein said eight or more marker proteins comprise HSP-27, phospho-ATF2 (Thr69), phospho-ATF2 (Thr71), Cortactin, phospho-Histone H3 (Thr3), phospho-EIF-4B (Ser422), phospho-Rpb1 (Ser2), phospho-Rpb1 (Ser5), and phospho-Cyclin-E (Thr62) together with at least one of cdc25C, phospho-cdc25C (Ser216), phospho-cdc25C (Thr48), and/or phospho-MAPKAPK-2 (Thr334).

10. The method of claim 1, wherein the expression and/or activity of all ten of said marker proteins is examined.

11. The method of claim 1, wherein said biological sample comprises a tumor sample, a blood sample, a bone marrow sample, or an effusion sample.

12. The method of claim 1, wherein the expression and/or activity of said one or more marker proteins is detected with a marker protein-specific antibody.

13. The method of claim 1, wherein the expression and/or activity of said one or more marker proteins that are phosphorylated is detected with a phosphorylation site-specific antibody.

14. The method of claim 1, wherein expression and/or activity of said one or more marker proteins is detected with a heavy isotope-labeled (AQUA) peptide corresponding a unique sequence on said marker protein(s).

15. The method of claim 1, wherein the expression and/or activity of said one or more marker proteins is determined in a whole cell assay.

16. The method of claim 15, wherein said whole cell assay is selected from the group consisting of immunohistochemistry (IHC), flow cytometry (FC), or immuno-fluorescence (IF).

17. The method of claim 1, wherein said cancer is selected from the group consisting of Small Cell Lung Cancer, Colorectal Cancer, Head and Neck Cancer, Ovarian Cancer, Melanoma, Renal Cell Carcinoma, Pancreatic Cancer and Non-Small Cell Lung Cancer.

\* \* \* \* \*